(12) United States Patent
Diamond et al.

(10) Patent No.: US 6,630,490 B2
(45) Date of Patent: Oct. 7, 2003

(54) METHODS FOR TREATMENT OF DISEASE-INDUCED PERIPHERAL NEUROPATHY AND RELATED CONDITIONS

(75) Inventors: Jack Diamond, Hamilton (CA); Alvin J. Glasky, Tustin, CA (US)

(73) Assignee: NeoTherapeutics, Inc., Irvine, CA (US)

( * ) Notice: Subject to any disclaimer, the term of this patent is extended or adjusted under 35 U.S.C. 154(b) by 0 days.

(21) Appl. No.: 09/900,844

(22) Filed: Jul. 6, 2001

(65) Prior Publication Data

US 2002/0055506 A1 May 9, 2002

Related U.S. Application Data

(60) Provisional application No. 60/216,844, filed on Jul. 7, 2000.

(51) Int. Cl.[7] .................... A61K 31/445; A61K 31/405; A61K 31/52
(52) U.S. Cl. ................... 514/315; 514/562; 514/415; 514/262
(58) Field of Search ................. 514/315, 562, 514/262, 415

(56) References Cited

U.S. PATENT DOCUMENTS

| | | |
|---|---|---|
| 3,300,380 A | 1/1967 | Gray et al. |
| 3,321,369 A | 5/1967 | Glasky et al. |
| 3,438,968 A | 4/1969 | Glasky et al. |
| 3,666,856 A | 5/1972 | Elion et al. |
| 4,035,486 A | 7/1977 | Laborit |
| 4,138,562 A | 2/1979 | Vince |
| 4,221,794 A | 9/1980 | Simon et al. |
| 4,221,909 A | 9/1980 | Simon et al. |
| 4,221,910 A | 9/1980 | Giner-Sorolla |
| 4,315,920 A | 2/1982 | Schaeffer et al. |
| 4,340,726 A | 7/1982 | Simon et al. |
| 4,347,360 A | 8/1982 | Ogilvie |
| 4,451,478 A | 5/1984 | Simon et al. |
| 4,643,992 A | 2/1987 | Goodman et al. |
| 4,952,693 A | 8/1990 | Sircar et al. |
| 5,023,244 A | 6/1991 | Goto et al. |
| 5,091,432 A | 2/1992 | Glasky |
| 5,093,318 A | 3/1992 | Goodman et al. |
| 5,187,162 A | 2/1993 | Marangos et al. |
| 5,237,051 A | 8/1993 | Garbers et al. |
| 5,256,677 A | 10/1993 | Sham et al. |
| 5,376,642 A | 12/1994 | Yarchoan et al. |
| 5,447,939 A * | 9/1995 | Glasky et al. ............... 514/310 |
| 5,565,437 A | 10/1996 | Marquez et al. |
| 5,595,901 A | 1/1997 | Rocancourt et al. |
| 5,795,756 A | 8/1998 | Johnson et al. |
| 5,801,159 A | 9/1998 | Miller et al. |
| 5,801,184 A | 9/1998 | Glasky et al. |
| 5,948,771 A | 9/1999 | Danziger |
| 6,027,936 A | 2/2000 | Glasky |

FOREIGN PATENT DOCUMENTS

| | | |
|---|---|---|
| WO | WO 91/14434 A1 | 10/1991 |
| WO | WO 96/03125 A1 | 2/1996 |
| WO | WO 96/20711 A1 | 7/1996 |
| WO | WO 94/33572 A1 | 9/1997 |
| WO | 99/56550 | 11/1999 |
| WO | WO 99/57119 | 11/1999 |
| WO | WO 99/57120 | 11/1999 |
| WO | WO 00/32197 A1 | 6/2000 |
| WO | WO 01/29039 A1 | 4/2001 |

OTHER PUBLICATIONS

B.R. Baker et al., *Nonclassical Antimetabolites XXII, Simulation of 5'–Phosphoribosyl Binding V. Inhibition of Succinoadenylate Kinosynthetase by 6–Mercapto–9–purinylalkanoic Acid Derivatives of 4– and 5–Aminosalicylic Acid, Journal of Pharmaceutical Sciences*, vol. 54, No. 11, Nov. 1965, pp. 1609–1616.

B.R. Baker et al., *Nonclassical Antimetabolites XXVII, Simulation of 5'–Phosphoribosyl Binding VII. Analogs of 6–Mercapto–9H–purine–9–ylpentanol Phosphate and Their Evaluation as Inhibitors of Succinoadenylate Kinosynthetase, Journal of Pharmaceutical Sciences*, vol. 54, No. 12, Nov. 1965, pp. 1774–1781.

M.P. Rathbone et al., *Physiology and Pharmacology of Natural and Synthetic Nonadenine–Based Purines in the Nervous System, Drug Development Research*, (1998) Wiley–Liss, Inc. pp. 354–372.

M. Holmes et al., *Induction of NGF–Dependent Nociceptive Nerve Sprouting in Adult Rate Skin by the Hypoxanthine Analogue AIT–082*, Dept. of Psychiatry and Behavioral Neurosciences, McMaster University Medical Centre, Hamilton, Ontario, Canada.

N.W. Tietz, ed., "Textbook of Clinical Chemistry" (W.B. Saunders Co., Philadelphia, 1986), pp. 882–886.

G.A. Lyles & B.A. Callingham, "The Effects of Thyroid Hormones on Monoamine Oxidase in the Rat Heart," *J. Pharm. Pharmacol.* 26: 921–930 (1974).

S.K. Gupta & R.K. Mishra, "Desensitization of $D_1$ Dopamine Receptors Down–Regulates the $G_s\alpha$ Subunit of G Protein in SK–N–MC Neuroblastoma Cells," *J. Mol. Neurosci.* 4: 117–123 (1993).

(List continued on next page.)

Primary Examiner—Theodore J. Criares
Assistant Examiner—Jennifer Kim
(74) Attorney, Agent, or Firm—Louis C. Cullman

(57) ABSTRACT

A method of treating disease-induced peripheral neuropathy comprises administering to a patient with disease-induced peripheral neuropathy an effective quantity of a purine derivative or analogue, a tetrahydroindolone derivative or analogue, or a pyrimidine derivative or analogue. If the compound is a purine derivative, the purine moiety can be guanine or hypoxanthine. The compound can induce peripheral nerve sprouting through the action of a neurotrophic factor such as nerve growth factor (NGF) without the occurrence of hyperalgesia. The peripheral nerve sprouting can be nociceptive nerve sprouting. The disease-induced peripheral neuropathy can be diabetic neuropathy or disease-induced peripheral neuropathy with another basis.

14 Claims, 8 Drawing Sheets

OTHER PUBLICATIONS

S.K. Gupta & R.K. Mishra, "Up–Regulation of $D_1$ Dopamine Receptors in SK–N–MC Cells After Chronic Treatment with SCH 23390," *Neurosci. Res. Commun.* 15: 157–166 (1994).

P.W. Baures et al., "Design, Synthesis, X–Ray Analysis, and Dopamine Receptor–Modulating Activity of Mimics of the 'C5' Hydrogen–Bonded Conformation in the Peptidomimetic 2–Oxo–3–(R)–[(2(S)–Pyrrolidinylcarbonyl)amino]–1–Pyrrolidineacetamide," *J. Med. Chem.* 37: 3677–3683 (1994).

J.E. Savelli et al., "Modulation of N–Methyl–D–Aspartate (NMDA) Antagonist–Induced Darting Behaviour by the Peptidomimetic PAMTA," *Brain Res.* 682: 41–49 (1995).

K.A. Jacobson, "Chemical Approaches to the Definition of Adenosine Receptors" in *Adenosine Receptors* (D.M.F. Cooper & C. Londos, eds., *Receptor Biochemistry and Methodology*, J.C. Venter, L.C. Harrison, eds., Alan R. Liss: New York, 1988), pp. 11:1–26.

S.H. Appel & J.L. McManaman, "Is a Breakdown of the Blood–Brain Barrier Cause or Effect?," *Neurobiol. Aging* 7:512–514 (1986).

S.M. MacDonald et al., "Immunological Parameters in the Aged and in Alzheimer's Disease," *Clin. Exp. Immunol.* 49:123–128 (1982).

A.E. Miller et al., "Immunological Studies in Senile Dementia of the Alzheimer Type: Evidence for Enhanced Suppressor Cell Activity," *Ann. Neurol.* 10:506–510 (1981).

K. Stefansson, "Neuroimmunology of Aging" in *Clinical Neurology of Aging* (M.L. Albert, ed., Oxford University Press, Oxford, (1984)), ch. 4, pp. 76–94.

L.R. Weitkamp et al., "Alzheimer Disease: Evidence for Susceptibility Loci on Chromosomes 6 and 14," *Am. J. Hum. Genet.* 35:443–53 (1983).

A. Yamazaki et al., Synthesis of Guanosine and Its Derivatives from 5–Amino–1–β–D–Ribofuranosyl–4–Imidazolecarboxamide I. Ring Closure with Benzoyl Isothiocyanate, *J. Org. Chem.* 32:1825–1828 (1967).

B. Alhede et al., "A Simple and Efficient Synthesis of 9–Substituted Guanines. Cyclodesulfurization of 1–Substituted 5–[(Thiocarbamoyl)amino]imidazole–4–carboxamides under Aqueous Basic Conditions," *J. Org. Chem.* 56:2139–2143 (1991).

R.E. Callard & A.J.H. Gearing, "The Cytokine Facts Book" (Academic Press, London, 1994), pp. 99–100, 104–105, 191–200, 235–237.

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44: 574–579 (1985).

F.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Effect of AIT–082, a Purine Analog, on Working Memory in Normal and Aged Mice," *Pharmacol. Biochem. Behav.* 47: 325–329 (1994).

A.J. Glasky et al., "Neurotrophins, Growth Factors and Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier Neurotrophins," *Brain Res.* 788: 87–94 (1998).

W.M. Pardridge, "CNS Drug Design Based on Principles of Blood–Brain Barrier Transport," *J. Neurochem.* 70: 1781–1792 (1998).

J.F. Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood–Brain Barrier," *Neurochem. Res.* 12: 791–796 (1987).

R. Spector, "Hypoxanthine Transport and Metabolism in the Central Nervous System," *J. Neurochem.* 50: 969–978 (1988).

D. Triguero et al., "Capillary Depletion Method for Quantitation of Blood–Brain Barrier Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols* (G.B. Irvine & C.H. Williams, eds., Humana Press, Totowa, NJ, 1997), pp. 353–360.

M.P. Rathbone et al., "Physiology and Pharmacology of Natural and Synthetic Nonadenine–Based Purines in the Nervous System," *Drug Develop. Res.* 45: 356–372 (1998).

M.P. Rathbone et al., AIT–082 as a Potential Neuroprotective and Regenerative Agent in Stroke and Central Nervous System Injury, *Exp. Opin. Invest. Drugs* 8: 1255–1262 (1999).

W.A. Banks et al., "Effects of Wheatgerm Agglutinin and Aging on the Regional Brain Uptake of HIV–1 gp120," *Life Sci.* 65: 81–89 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1998) (abstract).

O. Chu–LaGraff et al., "Effect of AIT–082 on Brain NGF mRNA Levels and Transport of AIT–082 Across the Blood–Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.H.J. Juurlink et al., "The Hypoxanthine Analogue AIT–082 Promotes Neurite Formation and Regeneration in Cultured Hippocampal Neurons," *Soc. Neurosci.* 24: 1941 (1998) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Acute Spinal Cord Crush Injury in Rats," *Soc. Neurosci.* 25: 1002 (1999) (abstract).

P. Di Iorio et al., "The Hypoxanthine Derivative AIT–082 Is Protective Against NMDA– or Kainic Acid–Induced Rat Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

G. Shaw et al., "Purines, Pyrimidines, and Glyoxalines. Part XIII. Some New Unambiguous Syntheses of 5–Aminoglyoxalines and 5–Aminoglyoxaline–4–carboxamides, and a Synthesis of 5–Amino–1–β–D–ribofuranosylglyoxaline–4–carboxyamide," *J. Chem. Soc. 1959:* 1648–(1959).

P.R. Birkett et al., "Synthesis and Intramolecular Cyclisation of 5–Aminoimidazolealkanoates and Their Conversion to Purine Derivatives," *Synthesis* 1991:157–159 (1991).

G.M. Blackburn & M.J. Gait, eds., *Nucleic Acids in Chemistry and Biology* (2d ed., Oxford University Press, 1996), pp. 148–152.

S. Lehmann et al., "Neurite Outgrowth of Neurons of Rat Dorsal Root Ganglia Induced by New Neurotrophic Substances with Guanidine Group," *Neurosci. Lett.* 152:57–60 (1993).

M. Barinaga, "Carbon Monoxide: Killer to Brain Messenger in One Step," *Science* 259:309 (1993).

A. Verma et al., "Carbon Monoxide: A Putative Neural Messenger," *Science* 259:381–384 (1993).

M. Zuo et al., "Nitric Oxide and Carbon Monoxide Produce Activity–Dependent Long–Term Synaptic Enhancement in Hippocampus," *Science* 260: 1946–1950 (1993).

Å. Seiger et al., "Intracranial Infusion of Purified Nerve Growth Factor to an Alzheimer Patient: The First Attempt of a Possible Future Treatment Strategy," *Behavioural Brain Res.* 57: 255–261 (1993).

A. Nitta et al., "Effects of Oral Administration of a Stimulator for Nerve Growth Factor Synthesis in Basal Forebrain–Lesioned Rats," *Eur. J. Pharmacol.* 250: 23–30 (1993).

M.H. Tuszynski & F.H. Gage, "Neurotrophic Factors and Neuronal Loss," *in Alzheimer Disease* (R.D. Terry et al., eds., Raven Press, New York, 1994), ch. 25, pp. 405–417.

R.D. Hawkins et al., "Nitric Oxide and Carbon Monoxide as Possible Retrograde Messengers in Hippocampal Long–Term Potentiation," *J. Neurobiol.* 25: 652–665 (1994).

S.H. Snyder, "NO and CO: The Body's Unprecedented Signaling Molecules," *1995 Yearbook of Science and The Future, Engyclopedia Britannica*, pp. 84–101.

J.Z. Fields et al., "Cardiac Muscarinic Cholinergic Receptors: Biochemical Identification and Characterization," *J. Biol. Chem.* 253:3251–3258 (1978).

D.H. Maurice & R.J. Haslam, "Molecular Basis of the Synergistic Inhibition of Platelet Function by Nitrovasodilators and Activators of Adenylate Cyclase: Inhibition of Cyclic AMP Breakdown by Cyclic GMP," *Mol. Pharmacol.* 37: 671–681 (1990).

I.D. Laviada et al., :Phosphatidylcholine–Phospholipase C Mediates the Induction of Nerve Growth Factor in Cultured Glial Cells, *FEBS Lett.* 364: 301–304 (1995).

A. Aurell et al., "The S–100 Protein in Cerebrospinal Fluid: A Simple ELISA Method," *J.Neurol. Sci.* 89: 157–164 (1989).

J. Barnett et al., "Human β Nerve Growth Factor Obtained from a Baculovirus Expression System Has Potent in Vitro and in Vivo Neurotrophic Activity," *Exp. Neurol.* 110:11–24 (1990).

M.M. Bradford, "A Rapid and Sensitive Method for the Quantitation of Microgram Quantities of Protein Using the Principle of Protein–Dye Binding," *Anal. Biochem.* 72: 248–254 (1976).

A. Dhainaut et al., "New Purines and Purine Analogs as Modulators of Multi–Drug Resistance," *J. Med. Chem.* 39:4099–4108 (1996).

U. Diederichsen & H.W. Schmidt, "β–Homoalanyl–PNA: A Special Case of β–Peptides with β–Sheet–Like Backbone Conformation; Organization in Higher Ordered Structures," *Eur. J. Org. Chem.* 1998: 827–835 (1998).

M. Iwakawa et al., "Synthetic Routes to Nucleoside Analogs of N–Substituted 1,3–Thiazolidines," *Can. J. Chem.* 56:326–335 (1978).

M.L. Peterson & R. Vince, "Synthesis and Biological Evaluation of 4–Purinylpyrrolidine Nucleosides," *J. Med. Chem.* 34:2787–2795 (1991).

D.A. Nugiel et al., "Facile Preparation of 2,6–Disubstituted Purines Using Solid Phase Chemistry," *J. Org. Chem.J. Org. Chem.* 62:201–203 (1997).

K.G. Estep et al., "Synthesis and Structure–Activity Relationships of 6–Heterocyclic–Substituted Purines as Inactivation Modifiers of Cardiac Sodium Channels," *J. Med. Chem.* 38:2582–2595 (1995).

R.E. Dolle & D. McNair, 9–(Sulfoximinoalkyl) Guanine Nucleosides as Potential Antiherpetic Agents,: *Tetrahedron Lett.* 34:1 (133–136) (1993).

S. Van Calenbergh et al., "Synthesis and Structure–Activity Relationship of Analogs of 2'–Deoxy–2'–(3–Methoxybenzamido)adenosine, a Selective Inhibitor of Trypanosomal Glycosomal Glyceraldehyde–3–Phospate Dehydrogenase," *J. Med. Chem.* 38:3838–3849 (1995).

D.L. Temple, Jrl, "Substituted 6,7–Dihydroimidazo[1,2–a] Purin–9 (4H)–ones," *J. Med. Chem.* 23:1188–1198 (1980).

Y. Mizuno et al., "Novel Protecting Group for the Synthesis of 7α–D–Pentofuranosylhypoxanthines," *J. Org. Chem.* 37:39–42 (1972).

P.K. Bridson & T.P. Wierich, "Cycle Homologues of Xanthines. I. Imidazo[4,5–e][1,4]Diazepine–5,8–Diones." *J. Heterocyclic Chem.* 25:1179–1182 (1988).

P. Jimonet et al., "Riluzole Series. Synthesis and in Vivo"Antiglutamate" Activity of 6–Substituted–2–benzothiazolamines and 3–Substituted 2–imino–benzothiazolines," *J. Med. Chem.* 42:2828–2843 (1999).

D. Manetti et al., "Design, Synthesis, and Preliminary Pharmacological Evaluation of 1,4–Diazabicyclo[4.3.0] nonan–9–ones as a New Class of Highly Potent Nootropic Drugs." *J. Med. Chem.* 43:1969–1974 (2000).

D. Manetti et al., "Molecular Simplification of 1,4–Diazabicyclo[4.3.0]nonan–9–ones Given Piperazine Derivatives That Maintain High Nootropic Activity," *J. Med. Chem.* 43:4499–4507 (2000).

P. Anand et al., "The Role of Endogenous Nerve Growth Factor in Human Diabetic Neuropathy," *Nature Medicine* 2:703–707 (1996).

S.C. Apfel et al. and the NGF Study Group, "Recombinant Human Nerve Growth Factor in the Treatment of Diabetic Polyneuropathy," *Neurology* 51:695–702 (1998).

J. Diamond et al., "NGF–Regulated Plasticity in the Adult Nervous System," *Soc. Neurosci. Abstr.* 14:245.6 (1988).

J. Diamond et al., "Evidence that Endogenous β Nerve Growth Factor is Responsible for the Collateral Sprouting, but not the Regeneration, of Nociceptive Axons in Adult Rats," *Proc. Natl. Acad. Sci. USA* 84:6596–6600 (1987).

J. Diamond et al., "Endogenous NCF and Nerve Impulses Regulate the Collateral Sprouting of Sensory Axons in the Skin of the Adult Rat," *J.Neurosci.* 12:1454–1466 (1992).

R. Doucette & J. Diamond, "Normal and Precocious Sprouting of Heat Nociceptors in the Skin of Adult Rats," *J. Comp. Neurol.* 261:592–603 (1987).

P.C. Jackson & J. Diamond, "Temporal and Spatial Constraints on the Collateral Sprouting of Low–Threshold Mechanosensory Nerves in the Skin of Rats," *J. Comp. Neurol.* 226:336–356 (1984).

S. Korsching & H. Thoenen, "Nerve Growth Factor Supply for Sensory Neurons: Site of Origin and Competition with the Sympathetic Nervous System," *Neurosci. Lett.* 54:201–205 (1985).

G.R. Lewin et al., "Nerve Growth Factor–Induced Hyperalgesia in the Neonatal and Adult Rat," *J. Neurosci.* 13:2136–2148 (1993).

G.R. Lewin et al., "Peripheral and Central Central Mechanisms of NGF–Induced Hyperalgesia," *Eur. J. Neurosci.* 6:1903–1912 (1994).

K.M. Mearow et al., "Increased NGF and mRNA Expression in Denervated Rat Skin," *NeuroReport* 4:351–354 (1993).

B.J. Nixon et al., "Impulse Activity Evokes Precocious Sprouting of Nociceptive Nerves into Denervated Skin," *Somatosensory Res.* 2:97–126 (1984).

E. Pertens et al., "Intraspinal and Behavioral Consequences of NGF–Induced Nociceptive Sprouting and NGF–Induced Hyperalgesia Compared in Adult Rats," *J. Comp. Neurol.* 410:73–89 (1999).

E. Theriault & J. Diamond, "Nociceptive Cutaneous Stimuli Evoke Localized Contractions in a Skeletal Muscle," *J. Neurophysiol.* 60:446–462 (1988).

D.R. Tomlinson et al., "Role of Neurotrophins in Diabetic Neuropathy and Treatment with Nerve Growth Factors," *Diabetes* 46 (Suppl. 2):S43–S49 (1997).

G.M. Yasargil et al., "Axonal Domains Within Shared Touch Domes in the Rat: A Comparison of Their Fate During Conditions Favoring Collateral Sprouting and Following Axonal Regeneration," *J. Comp. Neurol.* 270:301–312 (1988).

\* cited by examiner

Figure 2
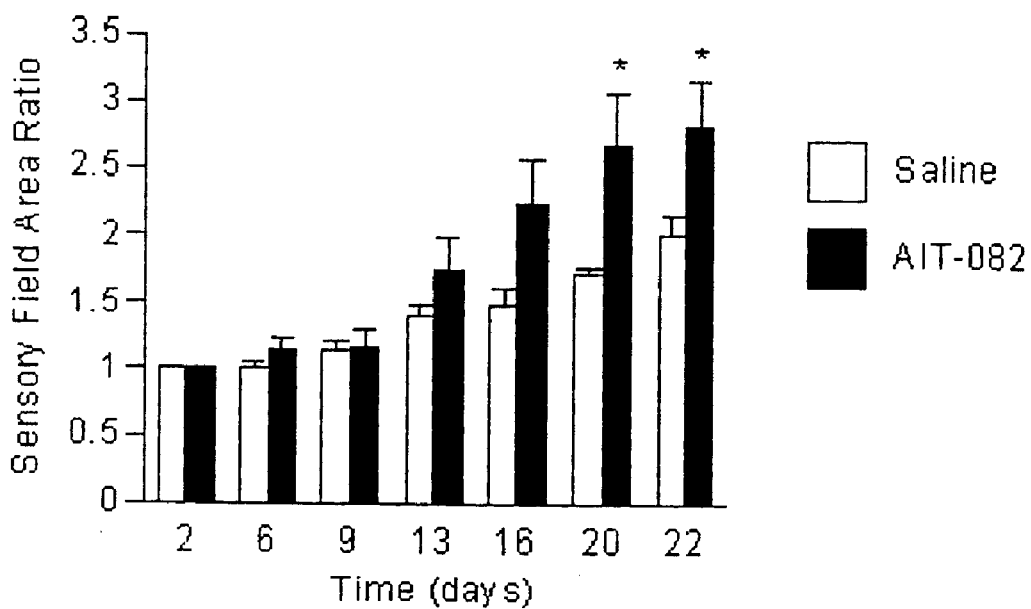
A
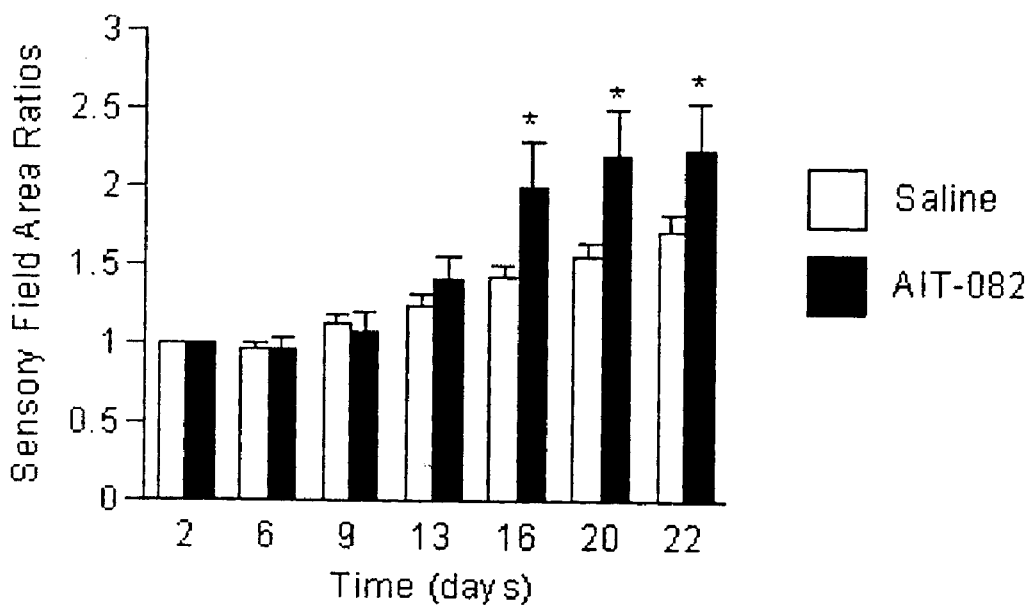
B

Figure 3. AIT-082 rescues sprouting blocked by a just-adequate anti-NGF treatment, but not when the anti-NGF dosage is increased.

Figure 4
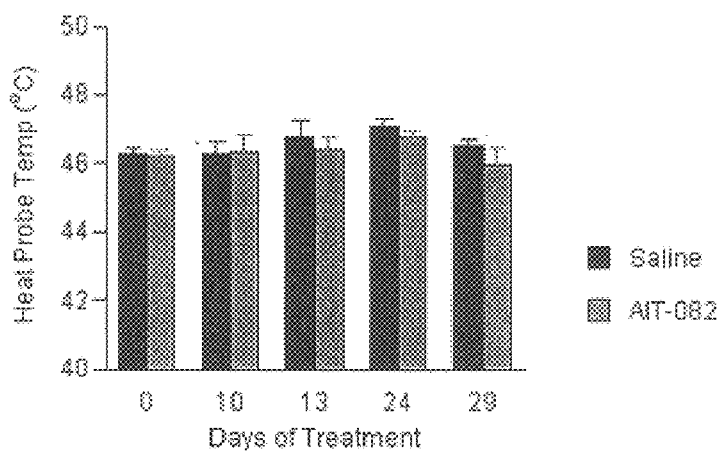
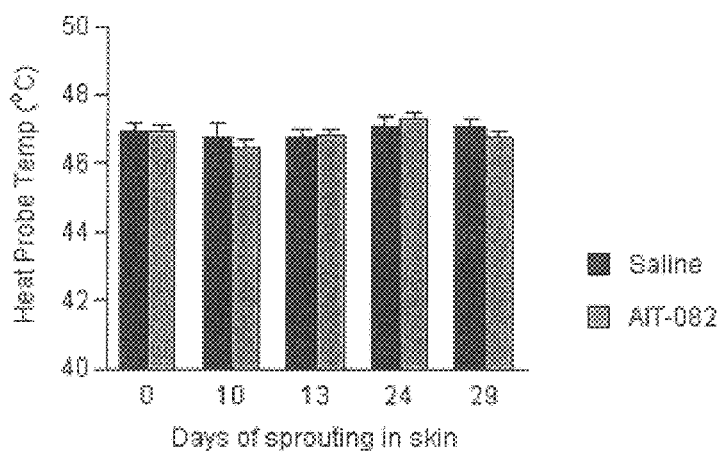
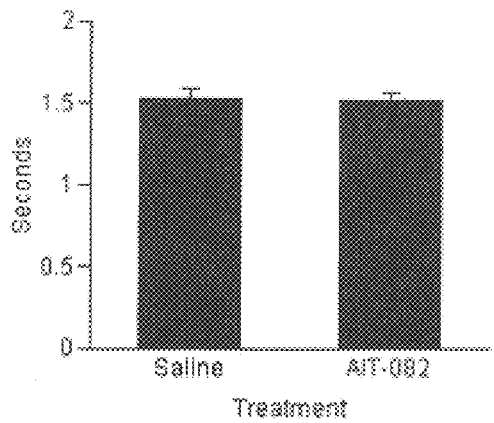

METHODS FOR TREATMENT OF DISEASE-INDUCED PERIPHERAL NEUROPATHY AND RELATED CONDITIONS

CROSS-REFERENCES

This application claims priority from Provisional Application Serial No. 60/216,844, filed Jul. 7, 2000 by Jack Diamond and Alvin J. Glasky, and entitled "Methods for Treatment of Peripheral Neuropathy and Related Conditions with Bifunctional Purine Analogues," which is incorporated herein in its entirety by this reference.

BACKGROUND OF THE INVENTION

This invention is directed to methods for treatment of disease-induced peripheral neuropathy and related conditions, particularly with purine derivatives or analogues, tetrahydroindolone derivatives or analogues, or pyrimidine derivatives or analogues.

Although methods have improved for the treatment of diabetes and its consequences, diabetic neuropathy is still an extremely serious problem. Diabetic neuropathy can be defined as a demonstrable disorder, either clinically evident or subclinical, that occurs in the setting of diabetes mellitus without other causes for peripheral neuropathy. The neuropathic disorder includes manifestations in the somatic and/or autonomic parts of the peripheral nervous system. Diabetic neuropathy often is associated with damage to the nerves just under the skin leading to one or more of the following conditions: numbness and tingling of fingers, hands, toes, and feet; weakness in hands and feet; or pain and/or burning sensation in hands and feet. Nerve damage as the result of peripheral neuropathy can also lead to problems with the GI tract, heart, and sexual organs, causing indigestion, diarrhea or constipation, dizziness, bladder infections, and impotence.

Diabetic neuropathy is one example of disease-induced peripheral neuropathy, which has other causes. Similar neuropathies can occur in conditions such as acromegaly, hypothyroidism, AIDS, leprosy, Lyme disease, systemic lupus erythematosus, rheumatoid arthritis, Sjögren's syndrome, periarteritis nodosa, Wegener's granulomatosis, cranial arteritis, and sarcoidosis, among other conditions.

More than 15% of the 13 million diabetic patients in the United States suffer symptomatic disturbances to the nervous system. Significant clinical neuropathy can develop within the first 10 years after diagnosis of diabetes and the risk of developing neuropathy increases the longer a person has diabetes. Although in most cases (30–40%) there are no symptoms, up to 60% of patients with diabetes have some form of neuropathy. Diabetic neuropathy appears to be more common in smokers, people over 40, and those who have had problems controlling their blood glucose levels.

There are currently no drugs on the market for the treatment of diabetic neuropathy. There are some drugs in trials or awaiting trials, including alond (zopolrestat; Pfizer), zenarestat (Fujisawa), pregabalin (Warner-Lambert), timcodar dimesylate (Vertex), the NMDA antagonist memantine (Merz), neurulin (Cortec), and an IGF-II product (Aurogen).

Other approaches are being tried or being considered, including aldose reductase inhibitors, which are thought to inhibit the increased flux through the polyol pathway caused by high blood glucose, mimicking the effect of improved glycemic control, nerve growth factor, alpha-lipoic acid, gamma-linolenic acid as a food supplement, insulin-like growth factor hormones, immunoglobulin, myo-inositol, or aminoguanidine.

However, there is still a substantial need for an improved treatment for diabetic neuropathy, particularly a treatment that can actually slow or reverse the degeneration of the nerves involved without inducing hyperalgesia.

Therefore, there exists a need for improved methods for treating diabetic neuropathy as well as other disease-induced peripheral neuropathies. There is a particular need for methods that can stimulate nerve growth or regeneration, particularly without inducing hyperalgesia.

SUMMARY

One embodiment of the present invention is a method of treating disease-induced peripheral neuropathy comprising administering to a patient with peripheral neuropathy an effective quantity of an effective quantity of a compound comprising: (1) a moiety A selected from the group consisting of a purine moiety, a purine analogue, a tetrahydroindolone moiety, a tetrahydroindolone analogue, a pyrimidine moiety, and a pyrimidine analogue; (2) a hydrocarbyl moiety L of 1 to 6 carbon atoms that is linked to the moiety A and that can be cyclic, with the hydrocarbyl moiety being optionally substituted with one or more substituents selected from the group consisting of lower alkyl, amino, hydroxy, lower alkoxy, lower alkylamino, lower alkylthio, and oxo; and (3) a moiety B that is linked to the moiety L though a carbonyl group wherein B is —OZ or N($Y_1$)-D, where Z is hydrogen, alkyl, aryl, heteroaryl, cycloalkyl, aralkyl, or heteroaralkyl; D is a moiety that promotes absorption of the compound; and $Y_1$ is hydrogen, alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms, which can be N, O, or S.

The purine moiety can be selected from the group consisting of hypoxanthine and guanine, as well as other purine moieties. A number of purine derivatives suitable for use in methods according to the present invention are disclosed. A particularly preferred purine derivative is N-4-carboxyphenyl-3-(6-oxohydropurin-9-yl) propanamide. Preferably, the compound is capable of passing through the blood-brain barrier.

Typically, the administration of the compound induces peripheral nerve sprouting in the skin of the patient to whom the purine derivative is administered. The peripheral nerve sprouting can be nociceptive nerve sprouting. Typically, the nociceptive nerve sprouting is induced without the occurrence of hyperalgesia. Additionally, methods according to the present invention can prevent large and small sensory nerve dysfunction in diabetes.

The disease-induced peripheral neuropathy can be diabetic neuropathy or can be a neuropathy associated with the following conditions: acromegaly, hypothyroidism, AIDS, leprosy, Lyme disease, systemic lupus erythematosus, rheumatoid arthritis, Sjögren's syndrome, periarteritis nodosa, Wegener's granulomatosis, cranial arteritis, or sarcoidosis.

BRIEF DESCRIPTION OF THE DRAWINGS

The following invention will become better understood with reference to the specification, appended claims, and accompanying drawings, where:

FIG. 2(a) is a graph showing the effect of AIT-082 on sprouting of heat-nociceptive nerve fibers;

FIG. 2(b) is a graph showing the effect of AIT-082 on sprouting of mechano-nociceptive nerve fibers;

FIG. 4(a) is a graph showing that AIT-082 does not cause hyperalgesia as measured by threshold temperature for foot withdrawal from a hot probe;

FIG. 4(b) is a graph showing that AIT-082 does not cause hyperalgesia as measured by threshold temperature for evoking the CTM reflex in dorsal skin;

FIG. 4(c) is a graph showing that AIT-082 does not cause hyperalgesia as measured by the latency of foot withdrawal from a 49° C. hot bath;

FIG. 8 is a graph showing the effect of AIT-082 on formalin-induced foot flinches in diabetic rats, showing the effect in phases 1, Q, and 2a.

DESCRIPTION

Figure 1:
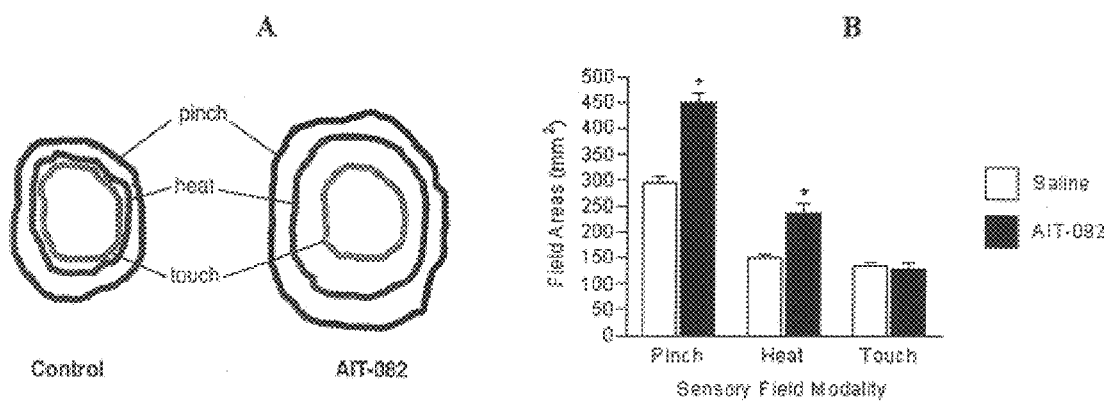
FIG. 1(a) is a sketch of maps of newly-isolated mDCN-T13 nerve fields, with the individual heat, pinch, and touch areas identified.
FIG. 1(b) is a graph showing the effect of AIT-082 on sprouting of nociceptive nerve fibers.

We have discovered that the bifunctional purine derivative N-4-carboxyphenyl-3-(6-oxohydropurin-9-yl) propanamide (also known as AIT-082 and leteprinim potassium), which bypasses the blood-brain barrier, can act to induce peripheral nerve sprouting in the skin of adult rats. As detailed below in the Example, this activity may be attributable to upregulation of cutaneous nerve growth factor (NGF) levels induced by this bifunctional purine derivative, although Applicants do not intend to be bound by this theory. Moreover, this activity occurred without the induction of hyperalgesia. This property of acting to induce peripheral nerve sprouting, therefore, should also be possessed by other purine derivatives and analogues, tetrahydroindolone derivatives and analogues, and pyrimidine derivatives and analogues, as discussed below. Methods according to the present invention can prevent large and small sensory nerve dysfunction in diabetes.

The peripheral nerve sprouting can be nociceptive nerve sprouting. The nociceptive nerve sprouting can occur without the induction of hyperalgesia.

Typically, a compound useful in a method of the present invention is capable of bypassing the blood-brain barrier.

More specifically, as detailed below in the Example, systematically administered AIT-082 closely mimics the effects both of increased levels of endogenous NGF, and of exogenous NGF. The compound induces vigorous collateral sprouting, and the sprouting it induced was blocked by systemic anti-NGF treatment. The growth of such nerve tissue is evoked and maintained entirely by the increased levels of NGF in adjacent denervated skin. However, AIT-082 resembles more the effects of increased endogenous NGF than of exogenous NGF, because it did not induce hyperalgesia.

Accordingly, one aspect of the present invention is a method of treating disease-induced peripheral neuropathy comprising administering to a patient with disease-induced peripheral neuropathy an effective quantity of a compound, the compound comprising: (1) a moiety A selected from the group consisting of a purine moiety, a purine analogue, a tetrahydroindolone moiety, a tetrahydroindolone analogue, a pyrimidine moiety, and a pyrimidine analogue; (2) a hydrocarbyl moiety L of 1 to 6 carbon atoms that is linked to the moiety A and that can be cyclic, with the hydrocarbyl moiety being optionally substituted with one or more substituents selected from the group consisting of lower alkyl, amino, hydroxy, lower alkoxy, lower alkylamino, lower alkylthio, and oxo; and (3) a moiety B that is linked to the moiety L though a carbonyl group wherein B is —OZ or N(Y$_1$)-D, where Z is hydrogen, alkyl, aryl, heteroaryl, cycloalkyl, aralkyl, or heteroaralkyl; D is a moiety that promotes absorption of the compound having activity against a multidrug transporter protein; and Y$_1$ is hydrogen, alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms, which can be N, O, or S.

Typically, a compound useful in a method of the present invention is capable of passing through the blood-brain barrier.

In one preferred embodiment of methods according to the present invention, the moiety A is a purine moiety.

In one alternative, A is a substituted or unsubstituted hypoxanthine moiety. Typically, in this alternative, L has the structure —(CH$_2$)$_n$ where n is an integer from 1 to 6.

The compound having the activity against disease-induced peripheral neuropathy can be a compound of formula (I)

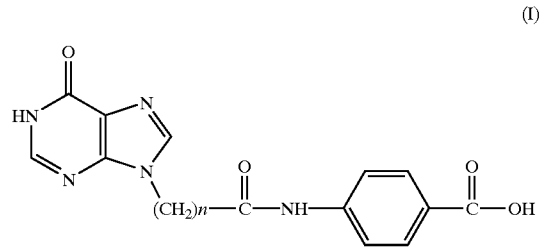

(I)

where n is an integer from 1 to 6 and R is hydrogen or lower alkyl or is a salt or prodrug ester of a compound of formula (I) wherein n is an integer from 1 to 6 and R is hydrogen or lower alkyl. Typically, the compound is a compound of formula (I) wherein n is an integer from 1 to 6 and R is hydrogen or lower alkyl. Typically, R is hydrogen, and the compound is N-4-[[3-(6-oxo-1,6-dihydropurin-9-yl)-1-oxopropyl] amino] benzoic acid, designated AIT-082. Alternatively, R is ethyl, and the compound is N-4-[[3-(6-oxo-1,6-dihydropurin-9-yl)-1-oxopropyl] amino] benzoic acid ethyl ester.

When the purine moiety is hypoxanthine, a preferred purine derivative is a compound of formula (I)

(I)

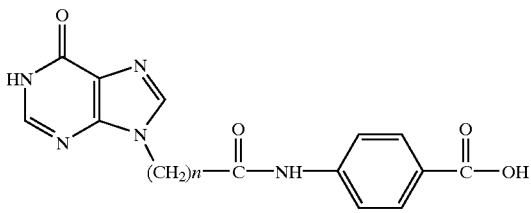

wherein n is an integer from of 1 to 6 or of a salt or prodrug ester of formula (1) wherein n is an integer from 1 to 6. Typically, the purine derivative is a compound of formula (I) wherein n is an integer from 1 to 6. Preferably, n is 2 and the compound is N-4-carboxyphenyl-3-(6-oxohydropurin-9-yl) propanamide, also known as AIT-082. The activity of this compound is described further in the Example.

Alternatively, the purine derivative can be a 9-substituted hypoxanthine derivative of formula (II)

(II)

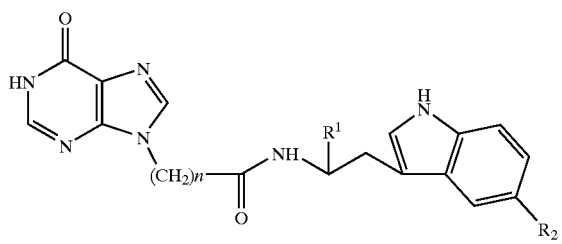

wherein n is a integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH.

In this alternative, for one particularly preferred purine derivative, n is 2, $R_1$ is H and $R_2$ is OH and the purine derivative is N-(2-(5-hydroxyindol-3-yl))ethyl-3-(6-oxohydropurine-9-yl) propanamide. In this alternative, for another particularly preferred purine derivative, n is 2, $R_1$ is H and $R_2$ is H and the purine derivative is N-(2-indol-3-yl) ethyl-3-(6-oxohydropurin-9-yl) propanamide. In this alternative, for still another particularly preferred purine derivative, n is 2, $R_1$ is COOH, and $R_2$ is OH and the purine derivative is N-(1-carboxyl-(2-(5-hydroxyindol-3-yl))ethyl-3-(6-oxohydropurin-9-yl) propanamide.

As another alternative, the purine derivative can be a 9-substituted hypoxanthine derivative of formula (III)

(III)

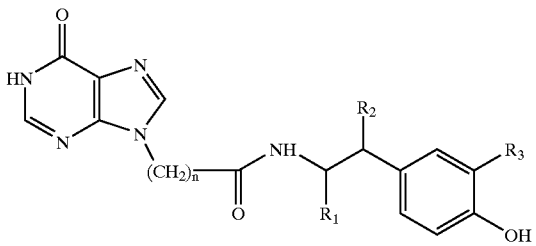

wherein n is an integer from 1 to 6, $R_1$ is selected from the group consisting of H, COOH, and $COOW_1$, wherein $W_1$ is selected from the group consisting of lower alkyl, amino, and lower alkylamino, $R_2$ is selected from the group consisting of H and OH, and $R_3$ is selected from the group consisting of H and OH.

In this alternative, for one particularly preferred purine derivative, n is 2, $R_1$ is H, $R_2$ is H, and $R_3$ is OH, and the purine derivative is N-(2-(3,4-dihydroxyphenyl))ethyl-3-(6-oxohydropurin-9-yl) propanamide. In this alternative, for another particularly preferred purine derivative, n is 2, $R_1$ is H, $R_2$ is OH, and $R_3$ is OH, and the purine derivative is N-(2-hydroxy-2-(3,4-dihydroxyphenyl))ethyl-3-(6-oxohydropurin-9-yl) propanamide. In this alternative, for still another particularly preferred purine derivative, n is 2, $R_1$ is COOH, $R_2$ is H, and $R_3$ is OH, and the purine derivative is N-(1-carboxyl-2-(3,4-dihydroxyphenyl))ethyl-3-(6-oxohydropurin-9-yl) propanamide.

When the purine moiety is guanine, one preferred purine derivative is a 9-substituted guanine derivative of formula (IV)

(IV)

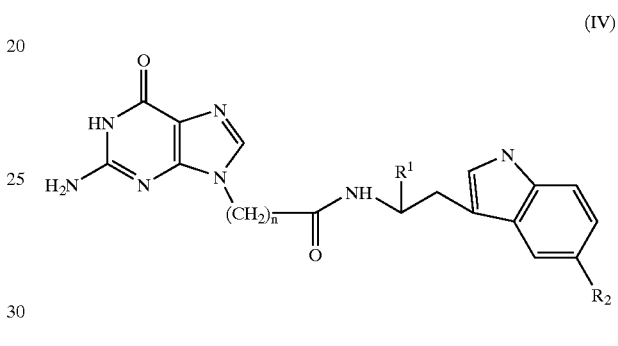

wherein n is an integer from 1 to 6, $R_1$ is selected from the group consisting of H, COOH, and $COOW_1$, or $W_1$ is lower alkyl, amino, or lower alkylamino, and $R_2$ is selected from the group consisting of H and OH.

In this alternative, for one particularly preferred purine derivative, n is 2, $R_1$ is H, and $R_2$ is OH, and the purine derivative is N-(2-(5-hydroxindol-3-yl))ethyl-3-(2-amino-6-oxohydropurin-9-yl) propanamide. In this alternative, for another particularly preferred purine derivative, n is 2, $R_1$ is H, and $R_2$ is H and the purine derivative is N-(2-(2-indol-3-yl)ethyl))-3-(2-amino-6-oxohydropurin-9-yl)) propanamide. In this alternative, for still another particularly preferred purine derivative, n is 2, $R_1$ is COOH, and $R_2$ is OH, and the purine derivative is N-(1-carboxyl)-(2-(5-hydroxyindol-3-yl))ethyl-3-(2-amino-6-oxohydropurin-9-yl) propanamide.

Alternatively, the purine derivative can be a 9-substituted guanine derivative of formula (V) wherein n is an integer from 1 to 6.

(V)

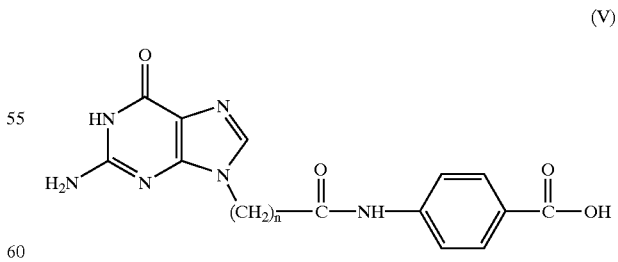

In this alternative, for one particularly preferred purine derivative, n is 2 and the compound is N-4-carboxyphenyl-3-(2-amino-6-oxohydropurin-9-yl) propanamide.

Alternatively, the purine derivative can be a 9-substituted guanine derivative of formula (VI) wherein n is an integer from 1 to 6.

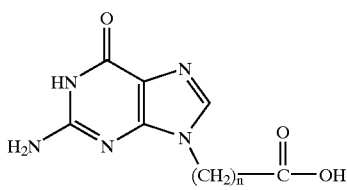

In this alternative, for one particularly preferred purine derivative, n is 2 and the compound is 3-(2-amino-6-oxohydropurine-9-yl) propanoric acid.

Alternatively, the purine derivative can be a 9-substituted guanine derivative of formula (VII) wherein n is an in integer from 1 to 6, p is an integer from 1 to 6, and q is an integer from 1 to 3.

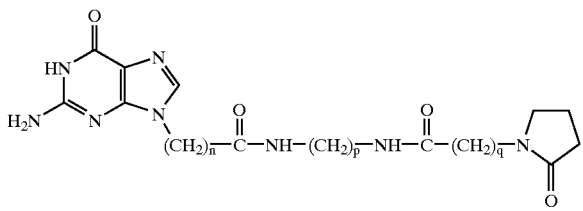

In this alternative, for one particularly preferred purine derivative, n is 2, p is 2, and q is 1, and the purine derivative is N-[2-[[2-(2-oxopyrrolidin-1-yl)-1-oxoethyl]amino]ethyl] propanamide.

Alternatively, the purine derivative can be a 9-substituted guanine derivative of formula (VIII) wherein $R_1$ is selected from the group consisting of H, COOH, and $COOW_1$, where $W_1$ is selected from the group consisting of lower alkyl, amino, and lower alkylamino, $R_2$ is selected from the group consisting of H and OH, and $R_3$ is selected from the group consisting of H and OH.

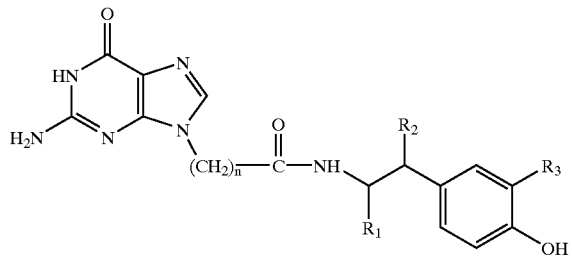

In this alternative, for one particularly preferred purine derivative, n is 2, $R_1$ is H, $R_2$ is H, and $R_3$ is OH, and the purine derivative is N-(2-(3,4-dihydroxyphenyl)ethyl-3-(2-amino-6-oxohydropurin-9-yl) propanamide. In this alternative, for another particularly preferred purine derivative, n is 2, $R_1$ is H, $R_2$ is OH, and $R_3$ is OH, and the purine derivative is N-(2-hydroxy-2-(3,4-dihydroxyphenyl) ethyl)-3-(2-amino-6-oxohydropurin-9-yl) propanamide. In this alternative, for still another particularly preferred purine derivative, n is 2, $R_1$ is COOH, $R_2$ is H, and $R_3$ is H and the compound is N-(1-carboxyl-2-(3,4-dihydroxyphenyl)ethyl)-3-(2-amino-6-oxohydropurin-9-yl) propanamide.

Alternatively, the purine derivative can be a 9-substituted guanine derivative of formula (IX) wherein n is an integer from 1 to 6 and p is an integer from 1 to 3.

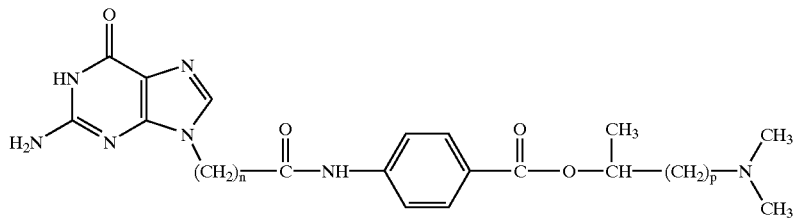

In this alternative, for one particularly preferred purine derivative, n is 2, p is 1, and the compound is the 1-(dimethylamino)-2-propyl ester of N4-carboxyphenyl-3-(2-amino-6-oxohydropurin-9-yl) propanamide.

Other bifunctional hypoxanthine derivatives suitable for use in methods according to the present invention are disclosed in U.S. Pat. No. 5,091,432 to Glasky, incorporated herein by this reference. Other bifunctional guanine derivatives suitable for use in methods according to the present invention are disclosed in U.S. patent application Ser. No. 09/419,153, by Glasky et al., incorporated herein by this reference.

More generally, purine-based compounds suitable for use in methods according to the present invention are compounds in which A is a substituted or unsubstituted 9-atom bicyclic moiety in which the 5-membered ring has 1 to 3 nitrogen atoms, the bicyclic moiety having the structure of formula (X)

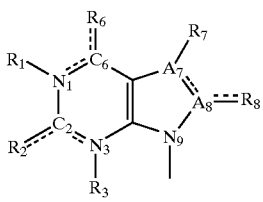

(X)

where:
(1) if the bond between $N_1$ and the bond between $C_5$ is a single bond, then the bond between $C_6$ and $R_6$ is a double bond, $R_6$ is O or S, and $R_1$ is hydrogen, alkyl, aralkyl, cycloalkyl, or heteroaralkyl;
(2) if the bond between $N_1$ and $C_6$ is a double bond, then the bond between $C_6$ and $R_6$ is a single bond, $R_1$ is not present, and $R_6$ is hydrogen, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;
(3) if the bond between $C_2$ and $N_3$ is a single bond, then the bond between $C_2$ and $R_2$ is a double bond, $R_2$ is O or S, and $R_3$ is hydrogen or alkyl;
(4) if the bond between $C_2$ and $N_3$ is a double bond, then the bond between $C_2$ is a single bond, $R_3$ is not present, and $R_2$ is hydrogen, alkyl, aralkyl, cycloalkyl, heteroaralkyl, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;
(5) $A_7$ and $A_8$ are C or N;
  (a) if $A_7$ and $A_8$ are both C and the bond between $A_7$ and $A_8$ is a single bond, then the bond between $A_8$ and $R_8$ is two single bonds to two hydrogen atoms or is a double bond in which $R_8$ is O or S and $R_7$ is two hydrogen atoms;
  (b) if $A_7$ and $A_8$ are both C and the bond between $A_7$ and $A_8$ is a double bond, then $R_7$ is hydrogen, the bond between $A_8$ and $R_8$ is a single bond and $R_8$ is hydrogen, halo, alkyl, alkenyl, aryl, aralkyl, aralkenyl, heteroaryl, heteroaralkyl, or heteroaralkenyl;
  (c) if $A_7$ and $A_8$ are both N, then the bond between $A_7$ and $A_8$ is a double bond, and $R_7$ and $R_8$ are not present;
  (d) if $A_7$ is C and $A_8$ is N, then the bond between $A_7$ and $A_8$ is a double bond, $R_7$ is hydrogen, and $R_8$ is not present;
  (e) if $A_7$ is N, $A_8$ is C, and the bond between $A_7$ and $A_8$ is a double bond, then $R_7$ is not present, the bond between $A_8$ is a single bond, and $R_8$ is hydrogen, halo, alkyl, alkenyl, aryl, aralkyl, aralkenyl, heteroaryl, heteroaralkyl, or heteroaralkenyl;
  (f) if $A_7$ is N, $A_8$ is C, and the bond between $A_7$ and $A_8$ is a single bond, then $R_7$ is hydrogen, alkyl, aryl, aralkyl, heteroaryl, or heteroaralkyl, the bond between $A_8$ and $R_8$ is a double bond, and $R_8$ is O or S; and
(6) $N_9$ is bonded to L; with the proviso that A does not have the structure of an unsubstituted guanine or hypoxanthine.

The purine moiety can be a purine moiety of formula (XI)

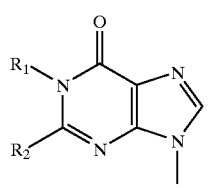

(XI)

in which:
(1) $R_1$ is selected from the group consisting of hydrogen, alkyl, aralkyl, cycloalkyl, and heteroaralkyl; and
(2) $R_2$ is selected from the group consisting of hydrogen, alkyl, aralkyl, cycloalkyl, heteroaralkyl, halo, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, arylkoxycarbonyl, heteroarylokoxycarbonyl, alkylaminocarbonyl, arylaminocarbonyl, heteroarylaminocarbonyl, aralkylaminocarbonyl, or heteroarylkylaminocarbonyl in which the alkyl portions could be cyclic and can contain from one to three heteroatoms which could be N, O, or S, with the proviso that both $R_1$ and $R_2$ are not hydrogen and that $R_1$ is not hydrogen when $R_2$ is amino.

The purine moiety of formula (XI) is a hypoxanthine or a guanine derivative but excludes unsubstituted hypoxanthine, in which $R_1$ and $R_2$ are hydrogen, and unsubstituted guanine, in which $R_1$ is hydrogen and $R_2$ is amino.

In one particularly preferred embodiment, $R_1$ is butyl and $R_2$ is hydrogen.

In another preferred embodiment, $R_1$ is benzyl and $R_2$ is hydrogen.

In another preferred embodiment, $R_1$ is dimethylaminoethyl and $R_2$ is hydrogen.

In another preferred embodiment, $R_1$ is cyclopentyl and $R_2$ is hydrogen.

In another preferred embodiment, $R_1$ is cyclohexylmethyl and $R_2$ is hydrogen.

In another preferred embodiment, $R_1$ is cyclopropylmethyl and $R_2$ is hydrogen.

In another preferred embodiment, $R_1$ is hydrogen and $R_2$ is phenyl.

In another preferred embodiment, $R_1$ is hydrogen and $R_2$ is trifluoromethyl.

In another preferred embodiment, $R_1$ is hydrogen and $R_2$ is butyl.

In another preferred embodiment, $R_1$ is butyl and $R_2$ is butyl.

In another preferred embodiment, $R_1$ is hydrogen and $R_2$ is methyl.

In another preferred embodiment, $R_1$ is hydrogen and $R_2$ is phenylamino.

Alternatively, the purine moiety is a purine moiety of Formula (XII)

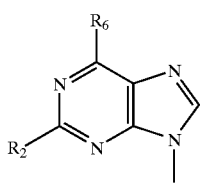

(XII)

in which:
(1) $R_2$ is selected from the group consisting of hydrogen, halo, amino, $OQ_3$, $SQ_3$, $NHNH_2$, $NHOQ_3$, $NQ_3Q_4$, or $NHQ_3$, where $Q_3$ and $Q_4$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, and heteroaralkylsulfonyl in which the alkyl portions can be cyclic and can contain from 1 to 3 heteroatoms which can be N, O, or S, and when $Q_3$ and $Q_4$ are present together and are alkyl, they can be taken together to form a 5- or 6-membered ring which can contain one other heteroatom which can be N, O, or S, of which the N can be further substituted with $Y_3$ where $Y_3$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaryloxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S; and (2) $R_6$ is selected from the group consisting of hydrogen, halo, amino, $OQ_5$, $SQ_5$, $NHNH_2$, $NHOQ_5$, $NQ_5Q_6$, or $NHQ_6$, where $Q_5$ and $Q_6$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, and heteroaralkylsulfonyl in which the alkyl portions can be cyclic and can contain from 1 to 3 heteroatoms which can be N, O, or S, and when $Q_5$ and $Q_6$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, heteroarylsulfonyl, aralkylsulfonyl, heteroaralkylsulfonyl, alkoxycarbonyl, aryloxycarbonyl, heteroaryloxycarbonyl, arylkoxycarbonyl, heteroarylkoxycarbonyl, alkylaminocarbonyl, arylaminocarbonyl, heteroarylaminocarbonyl, aralkylaminocarbonyl, or heteroaralkylaminocarbonyl in which the alkyl portions can be cyclic and can contain from 1 to 3 heteroatoms which can be N, O, or S.

In one preferred example of this embodiment, $R_2$ is hydrogen and $R_6$ is —$NH_2$ or —$N(CH_3)_2$.

In another preferred example of this embodiment, $R_2$ is hydrogen and $R_6$ is Cl.

In yet another preferred example of this embodiment, $R_2$ is —$NH_2$ and $R_6$ is Cl.

In another alternative, the purine moiety is the purine moiety of Formula (XIII)

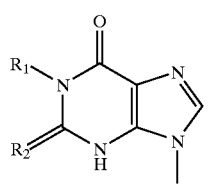

(XIII)

in which
(1) $R_1$ is hydrogen, alkyl, aralkyl, cycloalkyl, or heteroaralkyl; and
(2) $R_2$ is O or S.

Preferably, in this embodiment, $R_1$ is hydrogen and $R_2$ is O or S.

Particularly preferred purine-based compounds for use in methods according to the present invention include: (1) 4-[3-(1-benzyl-6-oxo-1,6-dihydropurin-9-yl)propionylamino] benzoic acid ethyl ester; (2) 4-[3-(1-butyl-6-oxo-1,6-dihydropurin-9-yl)propionylamino] benzoic acid ethyl ester; (3) 4-[3-(1-methyl-6-oxo-1,6-dihydropurin-9-yl) propionylamino] benzoic acid ethyl ester; (4) 4-[3-(1-(2-dimethylaminoethyl)-6-oxo-1,6-dihydropurin-9-yl) propionylamino] benzoic acid ethyl ester; (5) 4-[3-(2,6-dioxo-1,2,3,6-tetrahydropurin-9-yl)propionylamino] benzoic acid ethyl ester; (6) 4-[3-(6-methoxypurin-9-yl)

propionylamino] benzoic acid ethyl ester; (7) 4-[3-(6-dimethylaminopurin-9-yl)propionylamino] benzoic acid ethyl ester; (8) 4-[3-(2-amino-6-chloropurin-9-yl)propionylamino] benzoic acid ethyl ester; (9) 4-[2-(6-oxo-2-thioxo-1,2,3,6-tetrahydropurin-9-yl)propionylamino] benzoic acid ethyl ester; (10) 4-[2-(2-butyl-6-oxo-1,6-dihydropurin-9-yl)propionylamino]benzoic acid ethyl ester; (11) 4-[2-(6-oxo-2-phenyl-1,6-dihydropurin-9-yl) propionylamino]benzoic acid ethyl ester; (12) 4-{[3-(6-chloropurin-9-yl)propionyl]methylamino} benzoic acid methyl ester; (13) 3-(1-benzyl-6-oxo-1,6-dihydropurin-9-yl)-N-[3-(2-oxopyrrolidin-1-yl)propyl] propionamide; (14) 3-(1-benzyl-6-oxo-1,6-dihydropurin-9-yl)-N-{2-[2-(2-oxopyrrolidin-1-yl)acetylamino]ethyl} propionamide; (15) N-3-(2-oxopyrrolid in-1-yl)propyl]-3-(6-oxo-2-thioxo-1,2,3,6-tetrahydropurin-9-yl) propionamide; and (16) 3-(l-benzyl-6-oxo-1,6-dihydropurin-9-yl)-N-(3-morpholin-4-yl-propyl) propionamide.

In another alternative of methods according to the present invention, the compound is a tetrahydroindolone derivative or analogue where A is a 9-atom bicyclic moiety in which the 5-membered ring has one to three nitrogen atoms, the bicyclic moiety having the structure of formula (XIV)

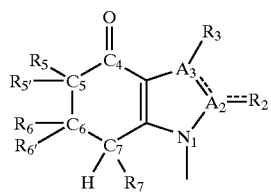

(XIV)

where (1) $N_1$ is bonded to L;

(2) $A_2$ and $A_3$ are C or N;

(a) If $A_2$ and $A_3$ are both C and the bond between $A_2$ and $A_3$ is a single bond, then the bond between $A_2$ and $R_2$ is two single bonds, two hydrogen atoms or is a double bond in which $R_2$ is O or S and $R_3$ is two hydrogen atoms;

(b) If $A_2$ and $A_3$ are both C and the bond between $A_2$ and $A_3$ is a double bond, then $R_3$ is hydrogen, the bond between $A_2$ and $R_2$ is a single bond and $R_2$ is hydrogen, halo, alkyl, alkenyl, aryl, aralkyl, aralkenyl, heteroaryl, heteroaralkyl, or heteroaralkenyl;

(c) If $A_2$ and $A_3$ are both N, then the bond between $A_2$ and $A_3$ is a double bond and $R_2$ and $R_3$ are not present;

(d) If $A_2$ is N and $A_3$ is C, then the bond between $A_2$ and $A_3$ is a double bond, $R_2$ is not present, and $R_3$ is hydrogen;

(e) If $A_2$ is C, $A_3$ is N, and the bond between $A_2$ and $A_3$ is a double bond, then $R_3$ is not present, the bond between $A_2$ and $R_2$ is a single bond, and $R_2$ is hydrogen, halo, alkyl, alkenyl, aryl, aralkyl, aralkenyl, heteroaryl, heteroaralkyl, or heteroaralkenyl;

(f) If $A_2$ is C, $A_3$ is N, and the bond between $A_2$ and $A_3$ is a single bond, then $R_3$ is hydrogen, alkyl, aryl, aralkyl, heteroaryl, or heteroaralkenyl, the bond between $A_2$ and $R_2$ is a double bond, and $A_2$ is O or S;

(3) $R_5$ is hydrogen, alkyl, aryl, aralkyl, heteroaryl, heteroaralkyl, alkanoyl, aroyl, heteroaroyl, aralkanoyl, heteroaralkanoyl, $NH_2$, $NHQ_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom, which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkyl-sulfonyl, alkoxycarbonyl, aryloxycarbonyl, heteroaryl-oxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(4) $R_{5'}$ is hydrogen unless $R_5$ is alkyl, in which case $R_5$ is hydrogen or the same alkyl as $R_5$;

(5) $R_5$ and $R_{5'}$ can be taken together as a double bond to $C_5$, and can be O, S, $NQ_3$, or C which can be substituted with one or two groups $R_5$, where $Q_3$ is alkyl, aralkyl, heteroaralkyl, aryl, heteroaryl, alkanoyl, aroyl, aralkanoyl, heteroaralkanoyl, or heteroaroyl, in which the alkyl portions can be cyclic and can contain from 1 to 3 heteroatoms which can be N, O, or S;

(6) $R_6$ is hydrogen, alkyl, aryl, aralkyl, heteroaryl, heteroaralkyl, $NH_2$, $NHQ_4$, $NQ_4Q_5$, OH, $OQ_4$, or $SQ_4$, where $Q_4$ and $Q_5$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_4$ and $Q_5$ are present together and are alkyl, they can be taken together to form a 5- or 6-membered ring which can contain one other heteroatom, which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(7) $R_{6'}$ is hydrogen unless $R_6$ is alkyl, in which case $R_{6'}$ is hydrogen or the same alkyl as $R_6$;

(8) $R_6$ and $R_{6'}$ can be taken together as a double bond to $C_6$ and can be O, S, $NQ_6$, or C which can be substituted with one or two groups $R_5$, and where $Q_6$ is alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S; and (9) $R_7$ is hydrogen unless $R_5$ is alkyl and $R_{5'}$ is hydrogen, in which case $R_7$ is the same alkyl as $R_5$.

Typically, A is a tetrahydroindolone moiety. More typically, the tetrahydroindolone moiety is a tetrahydroindolone moiety of formula (XV)

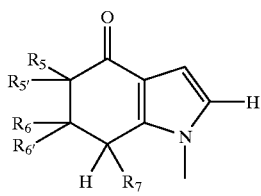

(XV)

in which (1) $R_5$ is hydrogen, alkyl, aryl, aralkyl, heteroaryl, heteroaralkyl, alkanoyl, aroyl, heteroaroyl, aralkanoyl, heteroaralkanoyl, $NH_2$, $NH_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, or heteroaroyl, in which the alkyl portions can be cyclic and can contain from one to three heteroatoms which can be N, O, or S;

(2) $R_{5'}$ is hydrogen;

(3) $R_6$ is hydrogen, alkyl, aryl, aralkyl, heteroaryl, heteroaralkyl, alkanoyl, aroyl, heteroaroyl, aralkanoyl, heteroaralkanoyl, $NH_2$, $NHW_1$, $NQ_1Q_2$, OH, $OQ_1$, or $SQ_1$, where $Q_1$ and $Q_2$ are aralkyl, heteroaralkyl, aryl, heteroaryl, alkanoyl, aroyl, aralkanoyl, heteroaralkanoyl, or heteroaroyl, in which the alkyl portions can be cyclic and can contain from one to three heteroatoms which can be N, O, or S and where $W_1$ is alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from one to three heteroatoms which can be N, O, or S;

(4) $R_{6'}$ is hydrogen; and (5) $R_7$ is hydrogen.

Typically, $R_5$, $R_{5'}$, $R_6$, $R_{6'}$, and $R_7$ are all hydrogen.

When A is a tetrahydroindolone moiety, preferred compounds are 4-[3-(4-oxo-4,5,6,7-tetrahydroindolon-1-yl) propionylamino] benzoic acid ethyl ester and 4-[3-(4-oxo-4,5,6,7-tetrahydroindolon-1-yl) propionylamino] benzoic acid.

In another alternative, the compound is a pyrimidine derivative or pyrimidine analogue. In this alternative, A is an amino-substituted 6-membered heterocyclic moiety of formula (XVI)

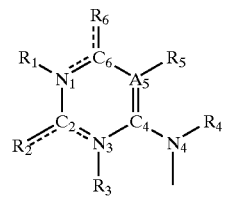

(XVI)

where (1) if the bond between $N_1$ and the bond between $C_6$ is a single bond, then the bond between $C_6$ and $R_6$ is a double bond, $R_6$ is O or S, and $R_1$ is hydrogen, alkyl, aralkyl, cycloalkyl, or heteroaralkyl;

(2) if the bond between $N_1$ and $C_6$ is a double bond, then the bond between $C_6$ and $R_6$ is a single bond, $R_1$ is not present, and $R_6$ is hydrogen, halo, amino, OH, $OQ_1$, $SQ_1$, $NHNH_2$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(3) if the bond between $C_2$ and $N_3$ is a single bond, then the bond between $C_2$ and $R_2$ is a double bond, $R_2$ is O or S, and $R_3$ is hydrogen or alkyl;

(4) if the bond between $C_2$ and $N_3$ is a double bond, then the bond between $C_2$ and $R_2$ is a single bond, $R_3$ is not present, and $R_2$ is hydrogen, alkyl, aralkyl, cycloalkyl, heteroaralkyl, halo, amino, OH, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_3$, where $Y_3$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(5) $R_4$ is hydrogen, alkyl, aralkyl, heteroaralkyl, alkanoyl, aroyl, heteroaroyl, aralkanoyl, heteroaralkanoyl, alkylsulfonyl, arylsulfonyl, heteroarylsulfonyl, alkoxycarbonyl, aryloxycarbonyl, heteroaryloxycarbonyl, alkylaminocarbonyl, arylaminocarbonyl, or heteroarylaminocarbonyl;

(6) $A_5$ is carbon or nitrogen;

(7) if $A_5$ is nitrogen, then $R_5$ is not present;

(8) if $A_5$ is carbon, then $R_5$ is hydrogen, amino, alkyl, alkoxy, halo, nitro, aryl, cyano, alkenyl, or alkaryl;

(9) if $R_5$ and $R_6$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S; and

(10) $N_4$ is bonded to L.

Typically, $A_5$ is carbon and the 6-membered heterocyclic moiety is a pyrimidine moiety.

When A is a pyrimidine moiety, in one alternative, $R_2$ is O and $R_3$ is hydrogen. In this alternative, the pyrimidine moiety can be cytosine, thymine, uracil, 3-methyluracil, 3-methylthymine, 4-methylcytosine, 5-methylcytosine, 5-hydroxymethylcytosine, 5-hydroxyuracil, 5-carboxymethyluracil, or 5-hydroxymethyluracil.

In another alternative, $R_2$ is S and $R_3$ is hydrogen. In this alternative, the pyrimidine moiety can be 2-thiouracil, 5-methylamino-2-thiouracil, 5-methyl-2-thiouracil, or 2-thiocytosine.

In still another alternative, $R_2$ is amino and the bond between $C_2$ and $N_3$ is a double bond. In this alternative, the pyrimidine moiety can be 2-aminopyrimidinone or 2-amino-4-chloropyrimidine.

In still another alternative, $R_2$ is hydrogen and the bond between $C_2$ and $N_3$ is a double bond. In this alternative, the pyrimidine moiety can be 4-chloropyrimidine, 5-amino-4-chloropyrimidine, 4-chloro-5-methylpyrimidine, 4-chloro-5-hydroxymethylpyrimidine, or 4-chloro-5-carboxymethylpyrimidine.

In still another alternative, $R_1$ is hydrogen, methyl, or ethyl, $R_5$ is hydrogen, methyl, or ethyl, and $R_6$ is O. In this alternative, the pyrimidine moiety can be pyrimidinone.

Particularly preferred pyrimidine compounds include: 4-[3-(2-amino-6-chloropyrimidin-4-ylamino) propionylamino] benzoic acid ethyl ester; 4-[3-(5-amino-6-chloropyrimidin-4-ylamino) propionylamino] benzoic acid ethyl ester; 4-[3-(6-chloropyrimidin-4-ylamino) propionylamino] benzoic acid ethyl ester; 4-[3-(2-amino-6-chloropyrimidin-4-ylamino) propionylamino] benzoic acid; 4-[3-(6-chloropyrimidin-4-ylamino) propionylamino] benzoic acid; 4-[3-(5-amino-6-chloropyrimidin-4-ylamino) propionylamino] benzoic acid; 3-[3-(2-amino-6-chloropyrimidin-4-ylamino) propionylamino] benzoic acid ethyl ester; 3-[3-(6-chloropyrimidin-4-ylamino) propionylamino] benzoic acid ethyl ester; 3-[3-(5-amino-6-chloropyrimidin-4-ylamino) propionylamino] benzoic acid ethyl ester; 3-[3-(2-amino-6-chloropyrimidin-4-ylamino) propionylamino] benzoic acid; 3-[3-(6-chloropyrimidin-4-ylamino) propionylamino] benzoic acid; and 3-[3-(5-amino-6-chloropyrimidin-4-ylamino) propionylamino] benzoic acid.

In accordance with the present invention, and as used herein, the following terms, when appearing alone or as part of a moiety including other atoms or groups, are defined with the following meanings, unless explicitly stated otherwise. In addition, all groups described herein can be optionally substituted unless such substitution is excluded. The term "alkyl," as used herein at all occurrences, refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "alkenyl," as used herein at all occurrences, refers to unsaturated groups which contain at least one carbon—carbon double bond and includes straight-chain, branched-chain, and cyclic groups, all of which can be optionally substituted. Preferable alkenyl groups have 2 to 10 carbon atoms. The term "alkoxy" refers to the ether —O-alkyl, where alkyl is defined as as above. The term "aryl" refers to aromatic groups which have at least one ring having a conjugated π-electron system and includes carbocyclic aryl and biaryl, both of which may be optionally substituted. Preferred aryl groups have 6 to 10 carbon atoms. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5–14 membered cyclic unsaturated radicals containing one, two, three, or four O, N, or S heteroatoms and having 6, 10, or 14 π-electrons delocalized in one or more rings, e.g., pyridine, oxazole, indole, thiazole, isoxazole, pyrazole, pyrrole, each of which can be optionally substituted as discussed above. The term "sulfonyl" refers to the group —S($O_2$)—. The term "alkanoyl" refers to the group —C(O)Rg, where Rg is alkyl. The term "aroyl" refers to the group —C(O)Rg, where Rg is aryl. Similar compound radicals involving a carbonyl group and other groups are defined by analogy. The term "aminocarbonyl" refers to the group —NHC(O)—. The term "oxycarbonyl" refers to the group —OC(O)—. The term "heteroaralkyl" refers to an alkyl group substituted with a heteroaryl group. Similarly, the term "heteroaralkenyl" refers to an alkenyl group substituted with a heteroaryl group. As used herein, the term "lower," in reference to an alkyl or the alkyl portion of an another group including alkyl, is defined as a group containing one to six carbon atoms. The term "optionally substituted" refers to one or more substituents that can be lower alkyl, aryl, amino, hydroxy, lower alkoxy, aryloxy, lower alkylamino, arylamino, lower alkylthio, arylthio, or oxo, in some cases, other groups can be included, such as cyano, acetoxy, or halo. The term "halo" refers generally to fluoro, chloro, bromo, or iodo; more typically, "halo" refers to chloro.

As indicated above, the linker L is a hydrocarbyl moiety of 1 to 6 carbon atoms that can be cyclic, with the hydrocarbyl moiety being optionally substituted with one or more substituents selected from the group consisting of lower alkyl, amino, hydroxy, lower alkoxy, lower alkylamino, lower alkylthio, and oxo. Preferably, the linker L has the structure —(CH$_2$)$_n$— wherein n is an integer from 1 to 6. As detailed below, for most preferred embodiments of compounds useful in methods according to the present invention, a preferred linker has n equal to 2 or 3.

The moiety B is either: (i) —OZ, where Z is hydrogen, alkyl, aryl, heteroaryl, cycloalkyl, aralkyl, or heteroaralkyl; or (ii) N(Y$_1$)-D, where D is a moiety that promotes absorption of the compound, and Y$_1$ is hydrogen, alkyl, aryl, heteroaryl, aralkyl, heteroaralkyl, which, when taken with D, can form a cyclic 5- or 6-membered saturated ring which can contain one other heteroatom which can be O, N, or S, of which N can be further substituted with Y$_2$, where Y$_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, heteroaralkylaminocarbonyl, in which the alkyl portions can be cyclic and can contain from 1 to 3 heteroatoms which can be N, O, or S. Typically, Y$_1$ is hydrogen. Where the moiety B is —OZ, the moiety B is a carboxylic acid or carboxylic acid or ester. Typically, where B is a carboxylic acid ester, the moiety Z is a lower alkyl, such as methyl, ethyl, butyl, propyl, or isopropyl.

In one alternative, the moiety D, as described above, is a moiety having at least one polar, charged, or hydrogen-bond-forming group to improve the metabolic and bioavailability properties of the compound. The moiety D can be, but is not limited to, a moiety with physiological or biological activity such as nootropic activity. In one alternative, the moiety D can be a moiety containing at least one carboxyl, carboxamide, carboxyl ester, or carbonyl function. In another alternative, the moiety D can be a moiety containing at least one hydroxyl, primary amino, secondary amino, tertiary amino, sulfhydryl, or sulfonamidyl function. The moiety D can be cyclic or acyclic. Preferred examples of the moiety D are described below.

When the moiety D is a cyclic or acyclic moiety containing at least one carbonyl, carboxamide, carboxyl ester, or carbonyl function, in one preferred example, D is a carboxylic acid or carboxylic acid ester with the structure

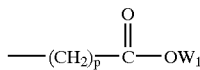

wherein p is an integer from 1 to 6 and W$_1$ is selected from the group consisting of hydrogen and lower alkyl. Typically, if W$_1$ is lower alkyl, it is methyl, ethyl, propyl, butyl, or isobutyl. Typically, p is 3. Typically, W$_1$ is hydrogen or ethyl.

In another preferred example, D and Y$_1$ are taken together to form a piperazine derivative as described in D. Manetti et al., "Molecular Simplification of 1,4-Diazabicyclo[4.3.0] nonan-9-ones Gives Piperazine Derivatives That Maintain High Nootropic Activity," *J. Med. Chem.* 43: 4499–4507 ("Manetti et al. (2000)"). B is an analogue of structure

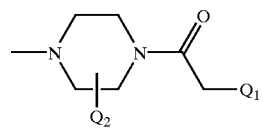

wherein Q$_1$ is hydrogen, methyl, ethyl, butyl, or propyl, Q$_2$ is hydrogen or methyl, where, if Q$_2$ is methyl, it can be located at either of the two possible positions in the piperazine ring.

In another preferred example, D has the structure

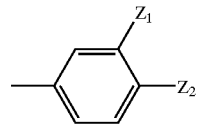

where one of Z$_1$ and Z$_2$ is hydrogen, and the other of Z$_1$ and Z$_2$ is —COOH or —COOW$_1$, wherein W$_1$ is alkyl. Typically, W$_1$ is selected from the group consisting of methyl, ethyl, propyl, butyl, and isobutyl. Either of Z$_1$ or Z$_2$ can be hydrogen. When Z$_1$ is hydrogen and Z$_2$ is —COOH, the moiety B is p-aminobenzoic acid (PABA). When Z$_1$ is —COOH and Z$_2$ is hydrogen, the moiety B is m-aminobenzoic acid (MABA). When Z$_1$ is hydrogen and Z$_2$ is —COOW$_1$, the moiety B is an ester of p-aminobenzoic acid (PABA). When Z$_1$ is —COOW$_1$ and Z$_2$ is hydrogen, the moiety B is an ester of m-aminobenzoic acid (MABA). Typically, these esters are ethyl esters.

When the moiety D is a moiety that contains at least one hydroxyl, primary amino, secondary amino, tertiary amino, sulfhydryl, or sufonamidyl function, in one preferred example, D is a phenylsulfonamidyl moiety of structure

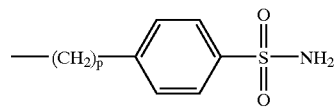

wherein p is an integer from 0 to 6. Typically, p is 2.

In another preferred example, D is an alkylpyridyl moiety of structure

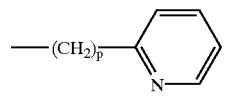

wherein p is an integer from 1 to 6. Typically, p is 1.

In another preferred example, D is a dialkylaminoalkyl moiety of the structure

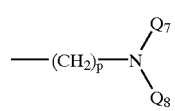

wherein p is an integer from 1 to 6 and Q$_7$ and Q$_8$ are alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S, and when Q$_1$ and Q$_2$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

Where $Q_7$ and $Q_8$ can be taken together to form a five or six member ring, the ring is typically pyrrolidine, piperidine, or morpholine. The pyrrolidine ring can be optionally substituted with oxo. The piperidine ring can be optionally substituted with methyl or ethyl. Typically, p is 2 or 3.

In another preferred example, D is an alkylpyrrolidine moiety of the structure

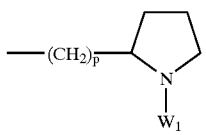

wherein p is an integer from 1 to 6 and $W_1$ is selected from the group consisting of methyl, ethyl, and propyl. Typically, $W_1$ is methyl. Typically, p is 2.

Preferably, a compound useful in methods according to the present invention has a log P of from about 1 to about 4 in order to optimize bioavailability and CNS penetration of the compound.

As detailed below in the Example, compounds used in methods according to the present invention are believed to exert their activity through the upregulation of neurotrophic factor synthesis. The upregulation of neurotrophic factor synthesis can involve one or more of these neurotrophic factors: NGF, NT-3, BDNF, and NT-4/5.

Exemplary studies and treatments were performed as discussed below using various dosages and routes of administration of selected exemplary compounds representative of compositions that are effective with the methods of the present invention. Of course, those skilled in the art will recognize that the present invention is not specifically limited to the particular compositions, dosages or routes of administration detailed below.

Depending upon the particular needs of the individual subject involved, the compositions used in the present invention may be administered in various doses to provide effective treatment concentrations based upon the teachings of the present invention. What constitutes an effective amount of the selected composition will vary based upon such factors including the activity of the selected compound, the physiological characteristics of the subject, the extent and nature of the subject's disease or condition and the method of administration. Exemplary treatment concentrations which have proven effective in modifying neural activity range from less than 1 μM to concentrations of 500 mM or more. Generally, initial doses will be modified to determine the optimum dosage for treatment of the particular mammalian subject. The compositions may be administered using a number of different routes including orally, topically, transdermally, intraperitoneal injection or intravenous injection directly into the bloodstream. Of course, effective amounts of the compounds may also be administered through injection into the cerebrospinal fluid or infusion directly into the brain, if desired.

The methods of the present invention may be effected using compounds administered to a mammalian subject either alone or in combination as a pharmaceutical formulation. Further, the compounds may be combined with pharmaceutically acceptable excipients and carrier materials such as inert solid diluents, aqueous solutions or non-toxic organic solvents. If desired, these pharmaceutical formulations may also contain preservatives and stabilizing agents and the like, as well as minor amounts of auxiliary substances such as wetting or emulsifying agents, as well as pH buffering agents and the like which enhance the effectiveness of the active ingredient. The pharmaceutically acceptable carrier can be chosen from those generally known in the art, including, but not limited to, human serum albumin, ion exchangers, dextrose, alumina, lecithin, buffer substances such as phosphate, glycine, sorbic acid, potassium sorbate, propylene glycol, polyethylene glycol, and salts or electrolytes such as protamine sulfate, sodium chloride, or potassium chloride. Other carriers can be used.

Liquid compositions can also contain liquid phases either in addition to or to the exclusion of water. Examples of such additional liquid phases are glycerin, vegetable oils such as cottonseed oil, organic esters such as ethyl oleate, and water-oil emulsions.

The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Formulations suitable for parenteral administration, such as, for example, by intravenous, intramuscular, intradermal, and subcutaneous routes, include aqueous and non-aqueous, isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solubilizers, stabilizers, and preservatives. Compositions suitable for use in methods according to the present invention can be administered, for example, by intravenous infusion, orally, topically, intraperitoneally, intravesically, or intrathecally. Formulations of compounds suitable for use in methods according to the present invention can be presented in unit-dose or multi-dose sealed containers, in physical forms such as ampules or vials.

The disease-induced peripheral neuropathy to be treated can be diabetic neuropathy or can be a peripheral neuropathy arising as the result of another condition, such as, but not limited to, acromegaly, hypothyroidism, AIDS, leprosy, Lyme disease, systemic lupus erythematosus, rheumatoid arthritis, Sjögren's syndrome, periarteritis nodosa, Wegener's granulomatosis, cranial arteritis, and sarcoidosis.

Although Applicants do not intend to be bound by this theory, the beneficial effects of bifunctional purine derivatives such as AIT-082 may depend on generalized trophic and NGF-sensitive mechanisms and not merely on the induction of sprouting. These trophic effects may boost the capacity of NGF-sensitive neurons to respond to still unknown regeneration factors other than NGF itself. For example, it is likely that CGRP and Substance P expression increases with treatment with AIT-082 or other bifunctional purine derivatives. Methods according to the present invention also can prevent large and small sensory nerve dysfunction in diabetes.

The invention is illustrated by the following Examples. These Examples are presented for illustration only and is not intended to limit the invention.

EXAMPLE 1

Administration of the Bifunctional purine Derivative N-4-Carboxyphenyl-3-(6-Oxohydropurin-9-yl) Propanamide Induces Nociceptive Nerve Sprouting The purpose of this study was to evaluate the effects of AIT-082 in the peripheral nervous system (PNS), focusing on well-characterized nerve growth factor (NGF)-dependent collateral sprouting of nociceptive nerves into denervated skin and within partially denervated skin (Nixon et al., 1984; Doucette and Diamond 1987). The induction and maintenance of this sprouting are brought about by endogenous NGF (Diamond et al., 1992), which increases in nerve-depleted skin both because of an increased NGF mRNA expression (Mearow et al., 1993), and because NGF is no longer taken up into eliminated nerve endings (Korsching and Thoenen, 1985). Systemically injected NGF induces sprouting in normal skin, enhances an on-going sprouting into adjacent denervated skin, and can restore a sprouting reduced by concomitant anti-NGF treatment (Diamond et al., 1992; Pertens et al., 1999). The clinical utility of exogenous NGF is severely limited because it causes hyperalgesia (Lewin et al., 1993, 1994). AIT-082 may up-regulate the expression of neurotrophic factors, including NGF. Thus we chose to examine the extent to which AIT-082 injections would mimic exogenous NGF, and if so, to discover if it's effects were due to a direct action on neurons, or via an AIT-082-induced up-regulation of endogenous NGF. Given that AIT-082 might have therapeutic applications and that exogenous NGF causes hyperalgesia we also examined whether its systemic administration induces hyperalgesia.

Methods

All the animal procedures used in these studies were approved by the Institutional Animal Research Ethics Board, and conform to NIH guidelines. In terminal experiments animals were sacrificed while anesthetized with sodium pentobarbitone, 45 mg/kg (injected intraperitoneally, or i.p.), which was used for all operative procedures and during electrophysiological recording sessions. The nociceptive field mappings were done using 35 mg/kg pentobarbitone, which allows the CTM reflex (see below) to be elicited while maintaining the anesthetic state.

"Isolation" of sensory fields: This procedure, the initial step in the study of collateral sprouting and was done as described in Diamond et al. (1992). Its purpose was to isolate the cutaneous innervation territory, or field, of a selected nerve within a vast surround of denervated back skin. The nerve used was the medial branch of the left dorsal cutaneous nerve (DCN), at segmental level T13 (mDCN-T13). The isolation of its field was achieved by surgically eliminating on the left side the 4 DCNs immediately rostral and caudal to DCN-T13 (respectively T9–T12 and L1–L4), the lateral branch of DCN-T13, and the 4 lateral cutaneous nerves supplying the flank skin adjacent to the DCN-T13 territory.

Mapping of sensory fields: As described in Nixon et al. (1984) and Doucette and Diamond (1987), the borders of the isolated mechano-nociceptive and heat-nociceptive fields, subserved respectively by the Aδ and C fibers mDCN-T13, were determined by systematically applying across the skin forceps pinches (for mechano-nociception) and brief applications of a 60° C. heat probe (for heat-nociception); the presence of nociceptive endings is indicated during these procedures when the stimuli elicit the "CTM reflex" response, a contraction of the underlying cutaneus trunci muscle, which causes a characteristic and easily recognized skin twitch (Theriault and Diamond, 1988). The low-threshold ("touch") fields were measured electrophysiologically as described by Jackson and Diamond (1984). The DCN-T13 was placed across bipolar platinum electrodes that fed into a preamplifier and thence to an oscilloscope and audio amplifier. Brushing innervated skin with a fine bristle generates impulses in the large myelinated Aβ axons, producing audible responses that disappear abruptly as the bristle crosses into denervated territory. The areas of the cutaneous territories of the three sensory modalities studied ("pinch", "heat" and "touch") were measured using the MCID image analysis system (Imaging Research, Inc., St. Catharines, Ontario, Canada).

Measurement of collateral sprouting: The collateral sprouting of pinch and heat fibers in the DCN-T13, and the axonal regeneration of these and of the touch (Aβ) axons which do not undergo collateral sprouting in adult animals (Jackson and Diamond, 1984; Yasargil et al., 1988) were measured by periodic field re-mappings. These re-mappings revealed the progressive expansion of the initially isolated mDCN-T13 nociceptive areas into the surrounding denervated skin as collateral sprouting proceeded (Nixon et al., 1984; Doucette and Diamond, 1987).

Detection of hyperalgesia: Nociceptive responses were studied in lightly restrained animals as described in Pertens et al. (1999), using the latency of foot withdrawal from a 49° C. footbath, the temperature of the footbath at which withdrawal was initiated, and the heat thresholds for evoking the "CTM" reflex from back skin (see above). Hyperalgesia is defined here as a lowering of the threshold of a nociceptive stimulus required to produce a reflex response, and/or a reduction in the latency of that response.

Administration of AIT-082: AIT-082 was obtained from NeoTherapeutics Inc., Irvine, Calif., USA. A 50 mg/ml solution in sterile 0.9% NaCl was made up freshly every three days. The standard administration protocol was a daily i.p. injection of 50 mg/kg AIT-082. A limited dose-response study (not illustrated) confirmed that this treatment was well above threshold for inducing nociceptive sprouting, but below saturating levels for this response.

Preparation of NGF and its antiserum: The preparation and purification of nerve growth factor (2.5S NGF or 7S NGF) from male mouse salivary glands and of anti-NGF antiserum (anti-NGF) from adult sheep, and the evaluation of potency in functional assays, were done as described in detail in Diamond et al. (1992).

Administration of anti-NGF antiserum: Subcutaneous injections were made in the groin region (not the region of back skin under study). The "low", or "adequate", dose anti-NGF treatment referred to later had a biological titer of 1:3,300, and was used at 0.3 ml/250 gm; the "high" or "supramaximal" anti-NGF had a titer of 1:10,000 and was used at 0.5 ml/250 gm.

Results

1. AIT-082 induces sensory nerve sprouting in normally innervated skin, but only of NGF sensitive fibers.

Here we report on whether AIT-082 would induce morphologically-demonstrable sprouting, and associated field expansions, within normally innervated skin. Two groups of unoperated rats were injected daily with either AIT-082 (50 mg/kg) or saline for 20 days. The innervation territory of mDCN-T13 was then isolated in each animal, as explained in Methods, to allow measurement of the two nociceptive areas of innervation (the heat field and the pinch field) by behavioral mapping, and the touch field, subserved by the NGF-insensitive Aβ fibers (Diamond et al., 1987) by electrophysiological mapping. The results are shown in FIG.

1a and 1b; the two nociceptive fields, pinch and heat, had expanded significantly in the animals receiving AIT-082 treatment, but the touch fields were unaffected.

2. AIT-082 enhances nociceptive sprouting into adjacent denervated skin.

This experiment examined whether the induction of sprouting by AIT-082 described above was additive to an on-going collateral sprouting into adjacent denervated skin. Immediately following the standard field isolation and mappings of the selected mDCN-T13 in two groups of rats, a daily regimen of AIT-082 injections was instituted in one group, with the second group receiving saline. The mappings were repeated every 3 or 4 days thereafter. Beginning at about 13 days post-isolation, an increased expansion of the nociceptive fields became apparent in the AIT-082 group relative to the expansions in the control group (FIG. 2). Because field expansions are represented here as a ratio (field area at the selected time relative to the initial field area), a direct comparison between this data and that of FIG. 1 is not possible. However, a comparison was achieved using the raw data that went to construct FIGS. 1 and 2; it showed that after 20 days of treatment, the amount by which the field expansions in the AIT-082 sprouting group exceeded the expansions in the controls was approximately equal to the expansion in field areas induced in unoperated animals after 20 days of AIT-082 treatment (shown in FIG. 1).

3. AIT-082 rescues a sprouting blocked by a just-adequate anti-NGF treatment, but not one blocked by a supramaximal treatment.

Figure 3:
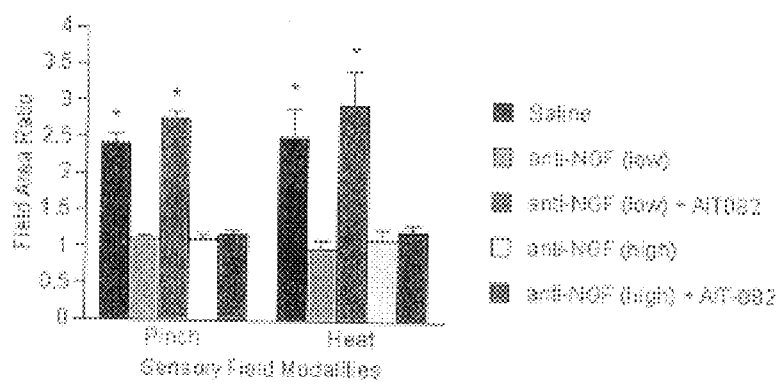
FIG. 3 is a graph showing the effect of AIT-082 in reversing the inhibition of sprouting by anti-NGF antibody.

The objective here was to discover how AIT-082-induced sprouting was affected by an anti-NGF treatment known to inhibit spontaneous collateral sprouting (Diamond et al., 1992). AIT-082 was administered daily throughout the period of a standard sprouting paradigm, exactly as in the experiment described in FIG. 2, but in this instance anti-NGF was also administered daily. In one group of animals the anti-NGF dosage was selected to be just adequate to block collateral sprouting on its own, while in a second group the anti-NGF dosage was about 5-fold this "threshold" dose (see Methods). The pinch and heat fields were measured after 22 days in all the animals. As seen in FIG. 3, AIT-082 totally rescued the sprouting that would otherwise have been blocked by the threshold ("low") anti-NGF treatment, but sprouting continued to be absent in the animals receiving the "supra-threshold" ("high") anti-NGF treatment.

4. AIT-082 does not cause hyperalgesia.

Groups of unoperated animals that had received the standard AIT-082 administration that caused nociceptive field expansions like those shown in FIG. 1 were examined at various times for the presence of hyperalgesia. As seen in FIG. 4, a number of recognized tests for hyperalgesia failed to provide any evidence for the occurrence of this phenomenon at any time during or following a treatment by AIT-082 that induced sprouting.

Discussion

AIT-082 promotes nociceptive sprouting by way of an up-regulation of endogenous NGF.

The present study shows firstly that systemically administered AIT-082 brings about a marked collateral sprouting of nociceptive nerves in adult rats, a sprouting normally driven entirely by skin-derived NGF (Diamond et al., 1992). However, AIT-082 does not evoke sprouting of the non-nociceptive Aβ sensory fibers, which are NGF-insensitive (Diamond et al., 1992). AIT-082 administration thus brings about a nociceptive hyper-innervation of the skin in unoperated animals, and enhances an on-going NGF-driven nociceptive sprouting into adjacent denervated skin. The absolute increase that AIT-082 produced in such an on-going sprouting was approximately equal to the amount of de novo sprouting (measured by the field expansion) it induced in the normally innervated skin of unoperated animals. In all these respects AIT-082 injections mimicked the effects of NGF injections (Diamond et al., 1992).

The second major finding is that the sprouting induced by AIT-082 is not achieved via a direct action on the nociceptive neurons, but is secondary to its action in up-regulating endogenous NGF levels. A block of spontaneous sprouting into adjacent denervated skin produced by a just-adequate anti-NGF treatment was completely reversed by administration of AIT-082, but AIT-082-induced sprouting was itself prevented when the anti-NGF dosage was increased approximately 5-fold.

Clinical Implications of the Present Findings.

There is increasing evidence that deficient neurotrophic support, including that provided to cutaneous nerves by NGF, contributes to the pathogenesis of the most common of peripheral neuropathies, diabetic neuropathy (Anand, 1996; Tomlinson et al., 1997), and indeed clinical trials of NGF as a treatment for this condition are already in progress (Apfel, 1998). Indirect support for this therapeutic approach comes from our earlier findings (Diamond et al., 1988; 1992) that chronic NGF-deprivation causes a shrinkage of nociceptive fields in the skin consistent with a "dying-back" neuropathy. AIT-082 administration, were it to induce endogenous NGF increases in the skin of diabetic individuals, could help protect NGF-sensitive neurons from the threat of diabetic neuropathy, without the hazard of hyperalgesia, as explained above.

References

The following references are cited in the Example.

Anand, P, Terenghi, G, Warner, G, Kaoperlman, P, Williams-Chestnut, R E, and Sinicropi, D V (1996) The role of endogenous nerve growth factor in human diabetic neuropathy. *Nature Medicine* 2:703–707.

Apfel, S. C., Kessler, J. S., Adornato, B. T., Litchy, W. J., Sanders, C., and Rask, C. S. (1998) Recombinant human nerve growth factor in the treatment of diabetic polyneuropathy. NGF Study Group. *Neurology* 51:695–702.

Diamond J, Holmes M and Visheau B (1988) NGF-regulated plasticity in the adult nervous system. *Soc Neurosci Abstr* 14:245.6

Diamond J, Coughlin M, MacIntyre L, Holmes M and Visheau B (1987) Evidence that endogenous nerve growth factor is responsible for the collateral sprouting, but not regeneration, of nociceptive axons in adult rats. *Proc Natl Acad Sci USA* 84:6596–6600.

Diamond J, Coughlin M and Holmes M (1992) Endogenous NGF and impulses regulate the collateral sprouting of sensory nerves in the skin of the adult rat. *J. Neurosci* 12:1454–1466.

Doucette R, Diamond J (1987) The normal and precocious sprouting of heat nociceptors in the skin of adult rats. *J. Comp. Neurol* 261:592–603.

Jackson P C, Diamond J (1984) Temporal and spatial constraints on the collateral sprouting of low-threshold mechanosensory nerves in the skin of rats. *J. Comp. Neurol* 226:336–345.

Korsching S, Theonen H (1985) Nerve growth factor supply for sensory neurons: site of origin and competition with the sympathetic nervous system. *Neurosci Lett* 54:201–205.

Lewin G R, Ritter A M, Mendell L M (1993) Nerve growth factor-induced hyperalgesia in the neonatal and adult rat. *J. Neurosci* 13:2136–2148.

Lewin G R, Rueff A, Mendell L M (1994) Peripheral and central mechanisms of NGF-induced hyperalgesia. *Eur J Neurosci* 6:1903–1912.

Mearow K M, Kril Y, and Diamond J (1993) Increased NGF mRNA expression in denervated rat skin. *Neuroreport* 4:351–354.

Nixon B J, Doucette R, Jackson P and Diamond J (1984) Impulse activity evokes precocious sprouting of nociceptive nerves into denervated skin. *Somatosensory Res* 2:97–126.

Pertens E, Urschel-Gybers B A, Holmes M, Pal R, Foerster A, Kri Y and Diamond J (1999) Intraspinal and behavioural consequences of NGF-induced nociceptive sprouting and NGF induced hyperalgesia compared in adult rats. *J Comp Neurol* 410:73–89.

Theriault E, Diamond J (1988) Nociceptive cutaneous stimuli evoke localized contractions in a skeletal muscle. *J Neurophysiol* 60:446–462.

Tomlinson D R, Fernyhough P and Diemel L T (1997) Role of neurotrophins in diabetic neuropathy and treatment with nerve growth factors. *Diabetes* 46 Suppl 2:S43–S49.

Yasargil G M, Macintyre L, Doucette $R_1$ Visheau B, Holmes M and Diamond J (1988) Axonal domains within shared touch domes in the rat: a comparison of their fate during conditions favoring collateral sprouting and following axonal regeneration. J Comp Neurol 270:301–312.

EXAMPLE 2

Administration of the Bifunctional Purine Derivative N-4-Carboxyphenyl-3-(6-Oxohydropurin-9-yl) Propanamide Prevents Sensory Nerve Dysfunction in Short-Term Diabetic Rats The aim of this study was to investigate the therapeutic potential of the purine analog AIT-082 in preventing nerve disorders that develop in diabetic rats.

Methods

All animal procedures were approved by the local animal subjects committee and were performed in accordance with NIH Guidelines on the Care and Use of Laboratory Animals.

Induction of diabetes: Female, adult, Sprague-Dawley rats (250–275 g) were fasted overnight prior to the intraperitoneal injection of a freshly made solution of streptozotocin in 0.9% saline to deliver a dose of 50 mg/kg body weight. Food was restored and animals left for 3 days before determination of glucose levels in a blood sample obtained by tail prick. Animals with blood glucose levels >15 mmol/l were considered diabetic and used in the study. Treatment with the AIT-082 began on the day that hyperglycemia was confirmed. Animals that did not present as diabetic at the first testing were re-dosed with streptazotocin and re-tested 3 days later. If they presented as diabetic then they were added to the study, if not they were omitted.

Blood and plasma glucose: Blood glucose was measured in freshly-obtained samples using a strip-operated reflectance meter (Glucostix and Glucocheck). At euthanasia, blood was collected by cardiac puncture and plasma extracted and stored at $-20°$ C. until subsequent measurement of glucose levels by spectrophotometric assay using the Trinder Kit (Sigma).

Nerve Conduction Velocity (NCV): Rats were anesthetized with halothane (4% in $O_2$ for induction, 2–3% for maintenance) and the sciatic nerve exposed via an incision in the flank followed by separation of underlying musculature by blunt dissection. A thermistor probe was placed adjacent to the nerve and the wound closed with a skin clamp and a second, rectal, probe was positioned. Nerve and rectal temperature was maintained at 37° C. by a heating lamp and thermal pad connected to a temperature regulator and the thermistor probes. The nerve was stimulated (single 5 v, 0.05 ms square wave pulse) by fine needle electrodes placed at the sciatic notch and Achilles tendon and the evoked EMG recorded from the interosseus muscles via two fine needle electrodes and displayed on a digital storage oscilloscope. The distance between the two sites of stimulation was measured using surface calipers and NCV calculated as the latency between the $A\alpha/\beta$ wave peaks of the M wave (MNCV) or H wave (SNCV) divided by the distance between the two stimulation sites. NCV measurements were made in triplicate and the median used to represent the NCV. The thermistor probes were removed, the skin incision closed with wound clips and coated with Betadine and the animal withdrawn from halothane and monitored until it recovers consciousness. Rats were then returned to their cages with free access to food and water.

Thermal response latency: Rats were placed in an observation chamber on the surface (floor temperature 30° C.) of a modified Hargreaves Apparatus (UARD, San Diego Calif.) and allowed to acclimate for 5 minutes. For measurement of thermal response latency, a heat source (delivering 4.5 amps to give a paw withdrawal latency of approximately 10 seconds in control rats) was maneuvered underneath the hind paw. The heat source was turned on manually and a stop clock activated until it shut off automatically when the paw was moved (24 sec cut off time). The procedure was repeated 4 times on the same paw at 5 minute intervals and the median of values 2–4 used to represent the thermal response latency.

Formalin test: Rats were restrained manually and formalin (50 $\mu$l of 0.2% solution) injected sub-dermally into the hindpaw dorsum. Rats were then placed in an observation chamber and flinching behaviors counted in 1 minute blocks every 5 minutes for 1 hour.

Results

General physiology: Diabetic rats were hyperglycemic at the end of the study and AIT-082 did not affect plasma glucose levels in either control or diabetic rats. Diabetes caused loss of body weight and this was not altered by AIT-082.

Figure 5:
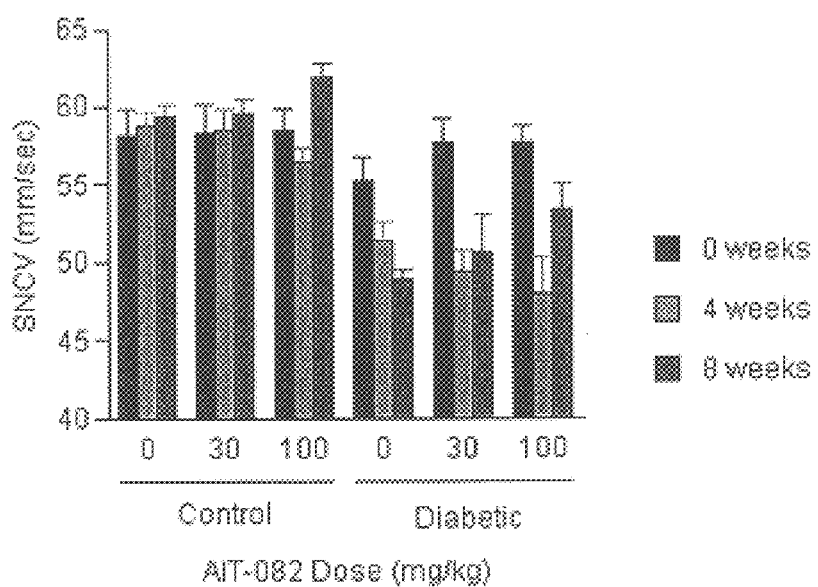
FIG. 5 is a graph showing the effect of AIT-082 on sensory nerve conduction velocity in control and diabetic rats.

SNCV (large sensory fiber): Diabetes reduced SNCV at weeks 4 and 8. AIT-082 had no effect in control rats or on the SNCV deficit at week 4. By week 8 there was a dose-dependent improvement of SNCV in diabetic rats treated with AIT-082 (FIG. 5).

Figure 6:
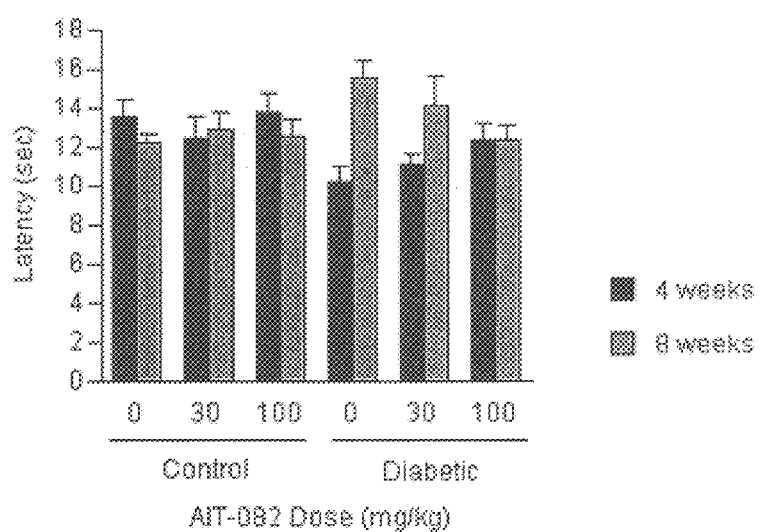
FIG. 6 is a graph showing the effect of AIT-082 on thermal response latency in control and diabetic rats.

Thermal response latency (small sensory fiber): Diabetes produced a transient thermal hyperalgesia at week 4 that progressed to hypoalgesia by week 8. AIT-082 was without effect in control rats. In diabetic rats, AIT-082 dose-dependently prevented both hyperalgesia and hypoalgesia. The high dose (100 mg/kg) completely prevented both hyperalgesia at week 4 and hypoalgesia at week 8 (FIG. 6).

Figure 7:
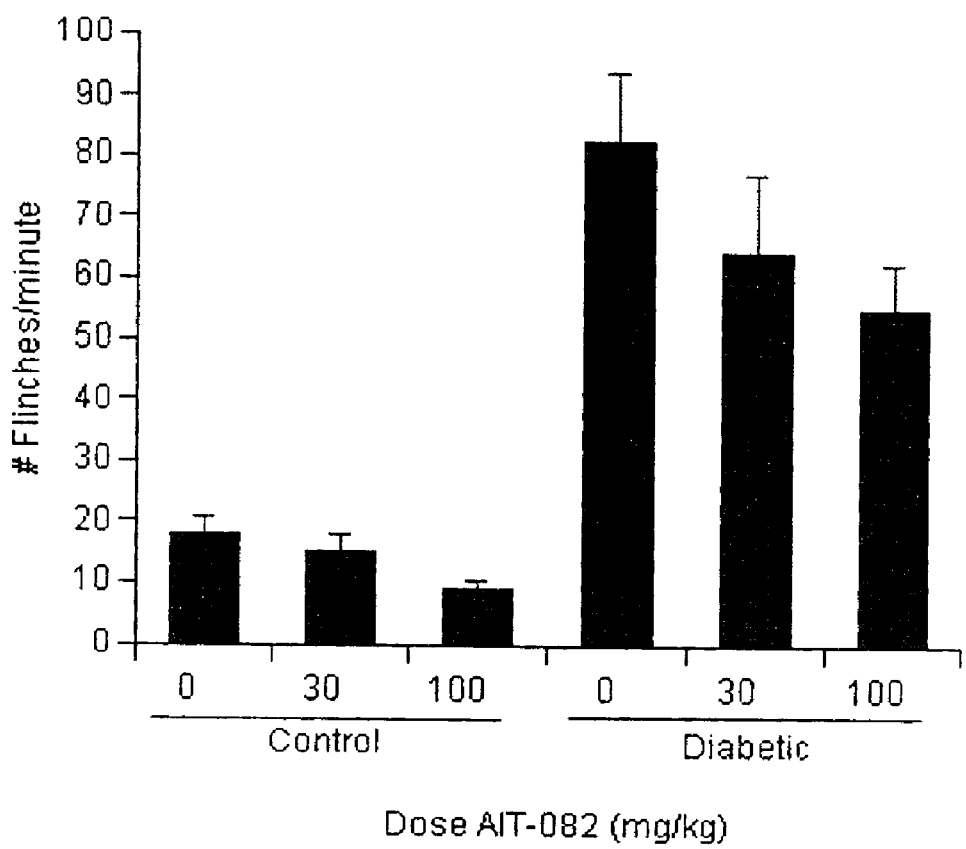
FIG. 7 is a graph showing the effect of AIT-082 on formalin-induced foot flinching in control and diabetic rats.
Figure 8:
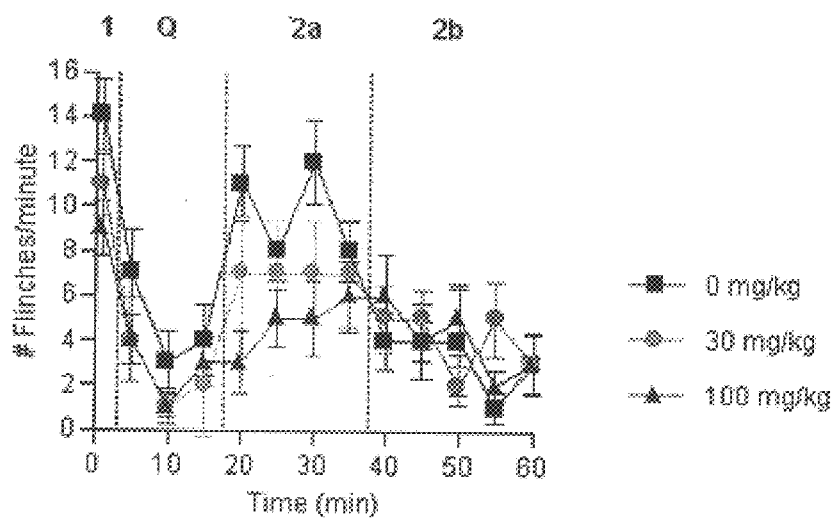

Formalin test (primary sensory neurons with spinal modulation): Diabetes produced marked hyperalgesia during the formalin test (FIG. 7). AIT-082 dose-dependently reduced formalin-evoked flinching in both control and diabetic rats. In diabetic rats the suppression of hyperalgesia was notable in phases 1, Q, and 2a (FIG. 8). These data suggest a general analgesic property of AIT-082 rather than any selectivity for diabetes-induced hyperalgesia.

Conclusion: AIT-082 prevented large and small sensory nerve dysfunction in short-term diabetic rats Advantages of the Invention The present invention provides new methods for treating patients with peripheral neuropathy, including diabetic neuropathy and other types of peripheral neuropathy, to induce peripheral nerve sprouting, which can include nociceptive nerve sprouting. These methods provide for nerve regeneration. These methods can be performed, at least in some alternatives, without inducing hyperalgesia. These methods can be combined with other treatments for peripheral neuropathy, including diabetic neuropathy, such as palliative measures for the relief of pain.

Although the present invention has been described in considerable detail, with reference to certain preferred versions thereof, other versions and embodiments are possible. Therefore, the scope of the invention is determined by the following claims.

We claim:

1. A method of treating disease-induced peripheral neuropathy comprising administering to a patient with disease-induced peripheral neuropathy an effective amount of a compound having activity against disease-induced peripheral neuropathy, the compound comprising a compound of formula (II)

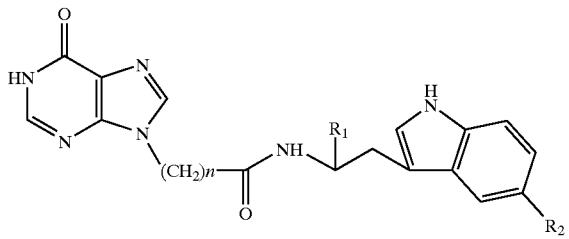

wherein n is an integer from 1 to 6, R is selected from the group consisting of H, COOH, and COOW$_1$, wherein W$_1$ is selected from the group consisting of lower alkyl, amino, and lower alkylamino, and R$_2$ is selected from the group consisting of H and OH.

2. The method of claim 1 wherein n is 2.

3. A method of treating disease-induced peripheral neuropathy comprising administering to a patient with disease-induced peripheral neuropathy an effective amount of a compound having activity against disease-induced peripheral neuropathy, the compound comprising a compound of formula (III)

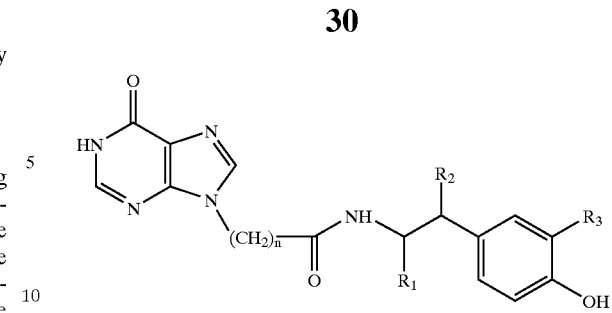

wherein n is an integer from 1 to 6, R$_1$ is selected from the group consisting of H, COOH, and COOW$_1$, wherein W$_1$ is selected from the group consisting of lower alkyl, amino, and lower alkylamino, R$_2$ is selected from the group consisting of H and OH, and R$_3$ is selected from the group consisting from the group consisting of H and OH.

4. The method of claim 3 wherein n is 2.

5. The method of claim 1 or 3 wherein the compound has a log P of from about 1 to about 4.

6. The method of claim 1 to 3 wherein the action of the compound having activity against disease-induced neuropathy is to induce upregulation of neurotrophic factor synthesis.

7. The method of claim 6 wherein the neurotrophic factor is selected from the group consisting of NGF, NT-3, BDNF, and NT-4/5.

8. The method of claim 1 or 3 wherein the administration of the compound having activity against disease-induced neuropathy induces peripheral nerve sprouting in the skin of the patient to whom the compound was administered.

9. The method of claim 8 wherein the peripheral nerve sprouting is nociceptive nerve sprouting.

10. The method of claim 9 wherein the nociceptive nerve sprouting is induced without the occurrence of hyperalgesia.

11. The method of claim 1 or 3 wherein the disease-induced peripheral neuropathy is a diabetic neuropathy.

12. The method of claim 11 wherein the administration of the compound having activity against diabetic neuropathy prevents large and small sensory nerve dysfunction.

13. The method of claim 1 or 3 wherein the peripheral neuropathy is caused by a condition other than diabetic neuropathy.

14. The method of claim 12 wherein the disease-induced peripheral neuropathy is caused by a condition selected from the group consisting of acromegaly, hypothyroidism, AIDS, leprosy, Lyme disease, systemic lupus erythematosus, rheumatoid arthritis, Sjögren's syndrome, periarteritis nodosa, Wegener's granulomatosis, cranial arteritis, and sarcoidosis.

* * * * *